US010000792B2

(12) United States Patent
Goueli et al.

(10) Patent No.: US 10,000,792 B2
(45) Date of Patent: Jun. 19, 2018

(54) METHODS FOR CYCLIC NUCLEOTIDE DETERMINATION

(75) Inventors: Said A. Goueli, Fitchburg, WI (US); Kuei-Hsuan Hsiao, Madison, WI (US); Meera Kumar, Verona, WI (US); Jolanta Vidugiriene, Madison, WI (US)

(73) Assignee: PROMEGA CORPORATION, Madison, WI (US)

( * ) Notice: Subject to any disclaimer, the term of this patent is extended or adjusted under 35 U.S.C. 154(b) by 849 days.

(21) Appl. No.: 12/710,087

(22) Filed: Feb. 22, 2010

(65) Prior Publication Data
US 2011/0129821 A1 Jun. 2, 2011

Related U.S. Application Data

(63) Continuation of application No. 11/634,756, filed on Dec. 6, 2006, now abandoned.

(60) Provisional application No. 60/742,922, filed on Dec. 6, 2005.

(51) Int. Cl.
C12Q 1/48 (2006.01)
C12Q 1/00 (2006.01)
C12Q 1/44 (2006.01)
C12Q 1/527 (2006.01)
C12Q 1/66 (2006.01)
G01N 33/74 (2006.01)

(52) U.S. Cl.
CPC ............ *C12Q 1/485* (2013.01); *C12Q 1/008* (2013.01); *C12Q 1/44* (2013.01); *C12Q 1/527* (2013.01); *C12Q 1/66* (2013.01); *G01N 33/74* (2013.01); *G01N 2333/16* (2013.01); *G01N 2333/726* (2013.01); *G01N 2333/916* (2013.01); *G01N 2333/988* (2013.01)

(58) Field of Classification Search
CPC combination set(s) only.
See application file for complete search history.

(56) References Cited

U.S. PATENT DOCUMENTS

| | | | |
|---|---|---|---|
| 4,234,681 A | 11/1980 | McElroy et al. | |
| 5,389,543 A | 2/1995 | Bunzow et al. | |
| 5,618,665 A | 4/1997 | Lurie et al. | |
| 5,759,787 A | 6/1998 | Strulovici et al. | |
| 5,795,756 A | 8/1998 | Roger et al. | |
| 6,001,553 A | 12/1999 | Broach et al. | |
| 6,150,503 A | 11/2000 | Pestka et al. | |
| 6,261,761 B1 | 7/2001 | Zhong et al. | |
| 6,569,617 B1 | 5/2003 | Wigler et al. | |
| 6,573,059 B1 | 6/2003 | Reymond et al. | |
| 6,632,621 B1 | 10/2003 | Lowery et al. | |
| 6,762,026 B1 | 7/2004 | Sugiyama et al. | |
| 6,893,827 B1 | 5/2005 | Palmer et al. | |
| 2004/0101922 A1 | 5/2004 | Somberg et al. | |
| 2007/0172896 A1 | 7/2007 | Goueli et al. | |

FOREIGN PATENT DOCUMENTS

| | | |
|---|---|---|
| JP | 2000-262296 | 9/2000 |
| JP | 2002533088 | 10/2002 |
| JP | 2003521941 | 7/2003 |
| WO | 03/106703 | 12/2003 |
| WO | WO 03/106703 | 12/2003 |
| WO | WO 2007/067557 | 6/2007 |

OTHER PUBLICATIONS

Kalderon et al, Localization of 3',5'-cyclic adenosine monophosphate phosphodiesterase (cAMP-PDEase) activity in isolated bovine thyroid plasma membranes. Histochemistry. 1980;65(3):277-89.*
Wang et al, The role of arachidonic acid in steroidogenesis and steroidogenic acute regulatory (StAR) gene and protein expression. J Biol Chem. Jun. 30, 2000;275(26):20204-9.*
Thompson et al, Cyclic adenosine 3':5'-monophosphate phosphodiesterase. Distinct forms in human lymphocytes and monocytes. J Biol Chem. Aug. 25, 1976;251(16):4922-9.*
Haque et al, Activation of phospholipase C and guanylyl cyclase by endothelins in human trabecular meshwork cells. Curr Eye Res. Dec. 1998;17(12):1110-7.*
Handa et al, Cyclic adenosine 3':5'-monophosphate in moss protonema: a comparison of its levels by protein kinase and gilman assays. Plant Physiol. Mar. 1977; 59(3):490-6.*
Bouchard et al, cAMP AlphaScreen™ Assay: A Method for the Pharmacological Characterization and Screening of Gαi-Coupled Receptors in Whole Cells. Perkin Elmer Life Sciences, Inc 2002.*
Shults et al, A multiplexed homogeneous fluorescence-based assay for protein kinase activity in cell lysates. Nat Methods. Apr. 2005;2(4):277-83. Epub Mar. 23, 2005.*
Chinese Patent Office Action for Application No. 200680052453.2 dated Feb. 1, 2011 (14 pages).
European Patent Office Search Report for Application No. 11075152.6 dated Feb. 3, 2012 (11 pages).
European Patent Office Search Report for Application No. 11005122.4 dated Feb. 3, 2012 (7 pages).
European Patent Office Extended Search Report for Application No. 11005122.4 dated Mar. 13, 2012 (14 pages).
Japanese Patent Office Action for Application No. 2008-544445 dated Mar. 15, 2012 (7 pages).

(Continued)

*Primary Examiner* — Sheridan Swope
(74) *Attorney, Agent, or Firm* — Michael Best & Friedrich LLP

(57) ABSTRACT

The present invention relates in general to cellular analysis tools and more particularly to methods for detecting or determining cyclic nucleotide concentrations in samples. Samples containing cyclic nucleotides may be contacted with a cyclic nucleotide-dependent protein kinase and a detection system which includes a substrate for the cyclic nucleotide-dependent protein kinase. The activities in cyclic nucleotide related pathways may be measured using the detection system.

11 Claims, 12 Drawing Sheets

(56) References Cited

OTHER PUBLICATIONS

DiscoveRx, "HitHunter™ FP Kinase Assay," web print-out dated Feb. 11, 2009 (2 pages).
DiscoveRx, "Kinase-Assays—non-antibody based," web print-out dated Feb. 11, 2009 (2 pages).
Goueli, S.A. et al., "A homogenous, high through-put luminescent cAMP assay to monitor modulation of G(s) and G(i) protein coupled receptors," Proc. Amer. Assoc. Cancer Res. (2006) 261-262, Database Biosis Abstract only, (Apr. 1, 2006).
Johnson, R.A. et al., "Analysis of adenosine 3',5'-monophosphate with luciferase luminescence," Anal. Biochem. (1970) 35(1):91-97.
Lehel, C. et al., "A chemiluminescent microtiter plate assay for sensitive detection of protein kinase activity," Anal. Biochem. (1997) 244(2):340-346.
Lonza Rockland, Inc., "PKLight™ HTS Protein Kinase Assay Manual," (2007) 4 pages.
Promega Corporation, "Kinase-Glo™ Luminescent Kinase Assay Technical Bulletin," (Oct. 2007) 21 pages.
Promega Corporation, "ProFluor PKA Assay Technical Buletin No. 315," (2002) 13 pages.
Promega Corporation, "ProFluor™ PKA Assay Technical Bulletin," (Sep. 2006) 17 pages.
Promega Corporation, "SignaTECT® cAMP-Dependent Protein Kinase Assay System Technical Bulletin," (Feb. 2006) 13 pages.
Rall, T.W. et al., "Formation of a cyclic adenine ribonucleotide by tissue particles," J. Biol. Chem. (1958) 232(2):1065-1076.
Titus, L. et al., "Glucocorticoids and 1,25-dihydroxyvitamin D3 regulate parathyroid hormone stimulation of adenosine 3',5'-monophosphate-dependent protein kinase in rat osteosarcoma cells," Endocrinology (1988) 123(3):1526-1534.
Vinade, L. et al., "Regulation of the phosphorylation state of the AMPA receptor GluR1 subunit in the postsynaptic density," Cell Mol. Neurobiol. (2000) 20(4):451-463.
Wikipedia, the Free Encyclopedia, "Crude Lysate," website, Dec. 16, 2009, retrieved from the Internet: http://en.wikipedia.org/w/index.php?title=Crude_lysate&oldid=332096097, retrieved on Mar. 8, 2008.
United States Patent Office Action for U.S. Appl. No. 11/634,756 dated Aug. 21, 2009 (8 pages).
United States Patent Office Action for U.S. Appl. No. 11/634,756 dated May 7, 2009 (15 pages).
United States Patent Office Action for U.S. Appl. No. 11/634,756 dated Nov. 12, 2008 (15 pages).
European Patent Office Action for Application No. 06848526.7 dated Aug. 17, 2009 (1 page).
European Patent Office Action for Application No. 06848526.7 dated Mar. 17, 2010 (4 pages).
Canadian Patent Office Action for Application No. 2632517 dated Aug. 12, 2010 (4 pages).
European Patent Office Action for Application No. 06848526.7 dated Oct. 6, 2010 (4 pages).
Indian Patent Office Action for Application No. 5226/DELNP/2008 dated Aug. 8, 2012 (3 pages).
Japanese Patent Office Action for Application No. 2008-544445 dated Aug. 9, 2012 (7 pages—with English Translation).
Goueli, S.A. et al., "A homogenous, high through-put luminescent cAMP assay to monitor modulation of G(s) and G(i) protein coupled receptors," Retrieved from http://www.promega.com/scientific_posters/ps036/ps036.pdf, 2009-03012 (also found at Proceedings of the American Association for Cancer Research Annual Meeting (2006) 47:261-262 and 97th Annual Meeting of the American Association for Cancer Research, Washington, DC (Apr. 1, 2005)).
Japanese Patent Office Action for Application No. 2008-544445 dated Feb. 28, 2013 (3 pages—with English Translation), "Remarks" only.
European Patent Office Search Report for Application No. 11075152.6 dated May 10, 2013 (5 pages).
European Patent Office Extended Search Report for Application No. 11005122.4 dated May 27, 2013 (5 pages).
Japanese Office Action for Application No. 2012-158962 dated Jan. 27, 2014 (8 pages, with English translation).
European Patent Office Supplementary Search Report and Office Action for Application No. 06848526.7 dated Mar. 12, 2009 (12 pages).
European Patent Office Search Report for Application No. 11075152.6 dated Sep. 28, 2012 (6 pages).
European Patent Office Extended Search Report for Application No. 11005122.4 dated Nov. 14, 2012 (5 pages).
Handa, A.K. et al., "Assay of adenosine 3',5' cyclic monophosphate by stimulatino of protein kinase: a method not involving radioactivity," Anal. Biochem. (1980) 102(2):332-339.
Rerm, M. et al., "High-throughput reporter gene assay for screening PDE4 inhibitors," Exp. Biol., Database Accession No. PREV200510325734 (2005) p. A861, Abstract only.
Goueli, S.A. et al., "A homogenous, high through-put luminescent cAMP assay to monitor modulation of G(s) and G(i) protein coupled receptors," Proc. Amer. Assoc. Cancer Res. (2006) 261-262, Database Biosis Abstract only.
Koresawa, M. et al., "High-throughput screening with quantitation of APT consumption: a universal non-radioisotope, homogeneous assay for protein kinase," Assay and Drug Dev. Tech. (2004) 2(2):153-154.
Weiss, B. et al., "Rapid microassay of adenosine 3',5'-monophosphate phosphodiesterase activity," Anal. Biochem. (1972) 45(1):222-235.
Buxbaum, J.D. et al., "A quantitative model for the kinetics of CAMP-dependent protein kinase (type 11) activity," J. Biol. Chem. (1989) 264(16):9344-9351.
Laurenza, A. et al., "Forskolin: a specific stimulator of adenylyl cyclase or a diterpene with multiple sites of action," Trends in Pharmacol. Sci. (1989) 10(11):442-447.
Japanese Patent Office Action for Application No. 2012-158962 dated Dec. 3, 2014 (5 pages, English translation included).
Wastila et al., "Measurement of Cyclic 3',5'-Adenosine Monophosphate by the Activation of Skeletal Muscle Protein Kinase," The Journal of Biological Chemistry, 1971, vol. 246, No. 7, 1996-2003.

* cited by examiner

A

|  | Dopamine | SKF38393 | Apomorphine | SKF82958 |
|---|---|---|---|---|
| $EC_{50}$: | 35.7nM | 78.1nM | 89.3nM | 23.4nM |

B

$EC_{50}$ (cAMP) = 0.0681 μM
$EC_{50}$ (cGMP) = 0.597 μM

A

B

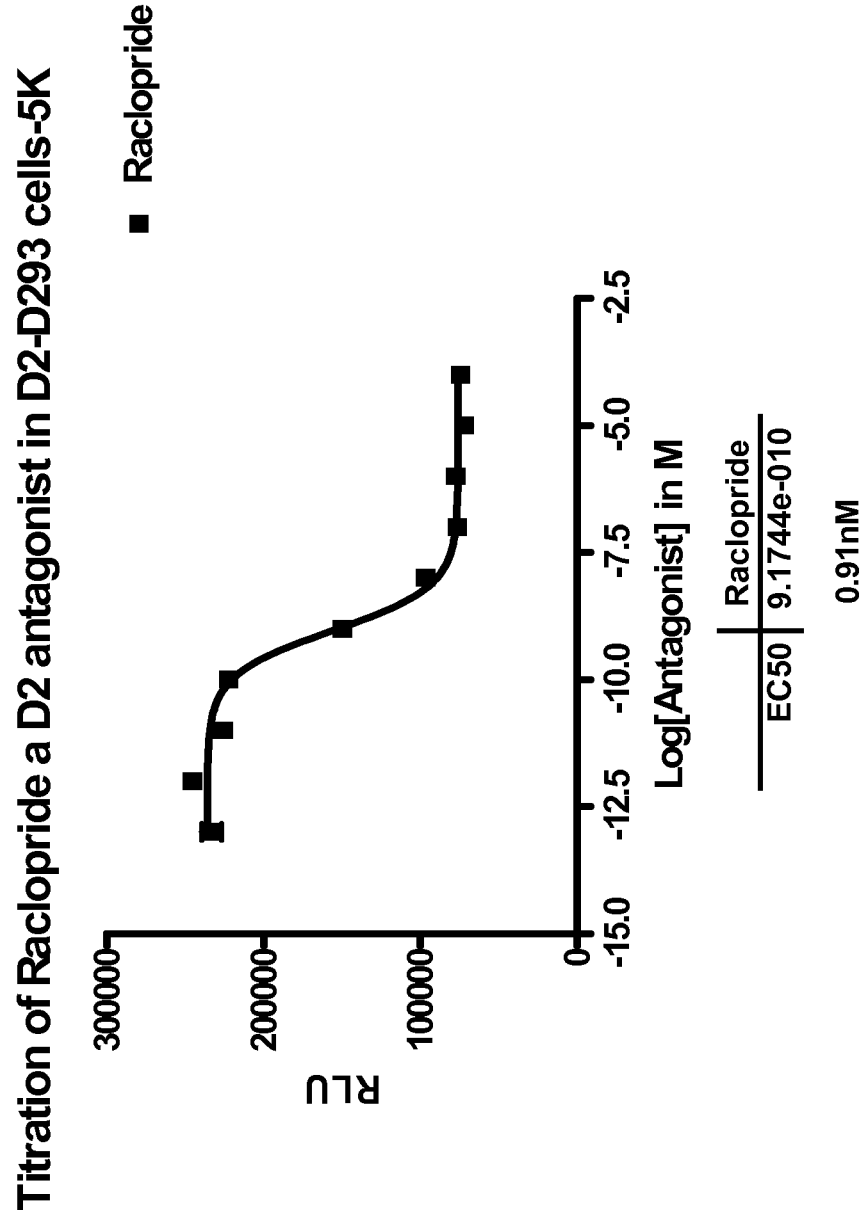

METHODS FOR CYCLIC NUCLEOTIDE DETERMINATION

CROSS-REFERENCE TO RELATED APPLICATIONS

This application is a continuation of U.S. application Ser. No. 11/634,756 filed Dec. 6, 2006 now abandoned, which claims the benefit of priority to U.S. Provisional Application No. 60/742,922 filed Dec. 6, 2005. These applications are each incorporated herein by reference in their entireties, for any purpose.

FIELD OF THE INVENTION

The present invention relates in general to cellular analysis tools and more particularly to methods for detecting or determining cyclic nucleotide concentrations in samples.

BACKGROUND OF THE INVENTION

The second messengers, adenosine 3',5' cyclic monophosphate (cAMP) and guanosine 3',5' cyclic monophosphate (cGMP), are important intracellular mediators of a variety of cellular functions including cell growth, differentiation, apoptosis, and cell death. Production of cAMP is controlled through the adenylyl cyclase family of enzymes, which convert adenosine triphosphate (ATP) to cAMP and inorganic pyrophosphate (PPi). The adenylyl cyclases are activated or inhibited via direct interaction with membrane bound G-protein coupled receptor (GPCR) α-subunits. When an α-subunit of a stimulatory GPCR is activated, designated $G_{\alpha s}$, adenylyl cyclase converts ATP to cAMP and PPi. Conversely, when an α-subunit of an inhibitory GPCR is activated, designated $G_{\alpha i}$, an inhibitory effect on adenylyl cyclase is exerted and the conversion of ATP to cAMP and PPi is not realized. G-protein coupled receptors play a prominent role in a wide variety of biological processes such as neurotransmission, cardiac output, and pain modulation. Their importance in developing new medically useful compounds is well understood; as such they are highly targeted in drug discovery research.

The intracellular concentration of cAMP is also affected by another group of enzymes, cyclic nucleotide phosphodiesterases (PDE), which catalyze the hydrolysis of cAMP to AMP and cyclic cGMP to GMP. Phosphodiesterases function in conjunction with adenylyl cyclases and guanylate cyclases to regulate the amplitude and duration of cell signaling mechanisms that are mediated by cAMP and cGMP. Phosphodiesterases therefore regulate a wide range of important biological responses to first messengers such as hormones, light, and neurotransmitters. There are two classes of PDEs; Class I are found in the cytoplasm or bound to intracellular organelles or membranes of all eukaryotic cells, whereas Class II PDEs are not well characterized and have only been found in lower eukayotes. Cellular responses controlled by Class I phosphodiesterases, through control of cAMP and cGMP conversion, include neuronal responses, aldosterone production, regulation of platelet aggregation, insulin regulation, emesis, regulation of smooth muscle tension, visual phototransduction, and modulation of T-cell responsiveness. Numerous clinically important compounds are known to inhibit phosphodiesterases including; rolipram, theophylline, and sildenafil. Therefore, inhibitors of phosphodiesterases are also important targets in drug discovery.

The second messenger cAMP is known to activate cAMP dependent protein kinase (PKA). Mammalian holo-PKA is a tetramer, made up of two regulatory and two catalytic subunits. cAMP binds to the regulatory subunits, thereby dissociating holo-PKA into its catalytic and regulatory subunits. Once released, the free catalytic subunits are capable of phosphorylating a multitude of cellular proteins, thereby causing changes in cellular functions such as muscle contraction, activation of cell cycle, activation of transcriptional activity, and DNA processing.

Because the activation or inhibition of GPCR and subsequent activation or inhibition of adenylyl cyclase results in an increase or decrease in intracellular cAMP, agents that affect their activity are important targets for drug discovery. Drugs that target GPCR account for many of the medicines sold worldwide due to the tremendous variety of biological processes relating to G-protein coupled receptors. Examples of drugs that influence GPCR include Claritin® and Alayert® (loratadine) which are used for relieving allergy symptoms, Paxil® (paroxetine HCl) for relief of depression, and Vasotec® (enalapril maleate) for relief of hypertension. Because of their importance, various GPCR assays have been developed to determine the effect of agonists and antagonists on these system components, mainly by assaying for the increase or decrease in cAMP levels. Limitations of these methods include non-homogeneous assays that require multiple dispensing steps, long incubation times, and the need for expensive equipment.

Therefore, what are needed are assays that require less manipulation than currently available technologies (e.g. two steps or less), assays that provide shorter incubation times (e.g., less than 1 hour), and assays that utilize low cost equipment while maintaining high throughput system (HTS) capabilities (e.g., luminescent based equipment). Such streamlining and cost effectiveness will allow for faster and easier evaluation of targets for drug discovery. Furthermore, luminescent based assays are not prone to interference from fluorescence; that is useful in screening large libraries of chemicals to discover the next potential drug.

SUMMARY OF THE INVENTION

The present invention relates in general to cellular analysis tools and more particularly to methods for detecting or determining cyclic nucleotide concentrations in samples.

Cyclic nucleotides, such as cAMP and cGMP, increase or decrease in response to a variety of substances that interact with cellular proteins. The methods described herein provide for the detection of such changes. In one embodiment, the methods described herein permit cyclic nucleotides to be detected and correlated with the effect of a stimulus on cellular proteins.

In one embodiment, methods as described herein monitor the binding of cyclic nucleotides to an enzyme that is dependent upon cyclic nucleotide binding in order to activate the enzyme (e.g. cAMP dependent protein kinase, or PKA). For example, once cAMP binds to PKA, PKA transfers a phosphate from adenoside triphosphate (ATP) to a suitable PKA substrate (e.g. Kemptide). The phosphorylation event is detected by various known methods, and the output of each detection method is correlated to the amount of cyclic nucleotide present in a sample. Suitable detection methods include, but are not limited to, methods based on luminescence, radioactivity, and fluorescence.

In one embodiment, a method to determine adenylyl cyclase activity in a sample is provided. Said method utilizes the activation of PKA to provide an activity that can be detected, measured and subsequently correlated to adenylyl cyclase activity. For example, if adenylyl cyclase is stimulated, cAMP is produced which activates PKA, whose activity is detected and correlated to adenylyl cyclase activity.

In another embodiment, a method to determine phosphodiesterase activity in a sample is provided. Said method utilizes the activation of PKA to provide an activity that is detected, measured, and subsequently correlated to phosphodiesterase activity. For example, if a phosphodiesterase is inhibited, cAMP is not converted to AMP or cGMP is not converted to cGMP, therefore cAMP and cGMP can activate PKA, whose activity is detected and correlated to phosphodiesterase activity.

In further embodiments, methods for monitoring the activation of a G-protein coupled receptor (GPCR) by an agonist, or its inhibition by an antagonist, are provided. For example, the level of cAMP found upon addition of agonist or antagonist to a sample comprising a GPCR is detected and measured through the activation of PKA. Such activity (or lack thereof) is detected by a measurable output that is correlated to cAMP levels or amounts.

In one embodiment, samples used in practicing the methods as described herein comprise a lysate. In some embodiments, the sample lysate is derived from prokaryotes or eukaryotes such as bacteria, yeast or mammalian cells. In some embodiments, said sample comprises plasma membranes, cellular membranes, and/or organellar membranes. Membrane preparations as described herein have furnished unexpected results, such that the membrane preparations maintain the integrity and functionality of processes, proteins and receptors (Examples 9-11) associated with the membranes. This allows for targeted membrane functional assays to be performed using the methods as described herein, without accompanying cell lysate components found in a normal cell lysate.

Measurable output may be in the form of bioluminescence, chemiluminescence, radioactivity, or differential output based on different fluorescence technologies (e.g. fluorescence polarization, fluorescence resonance energy transfer, and immunoassay). In one embodiment, the measurable output is in the form of bioluminescence. For example, the coleopteran (firefly) luciferase enzyme utilizes ATP and other factors to convert beetle luciferin to oxyluciferin, a byproduct of the reaction being light. Once PKA is activated, the amount of PKA activation is dependent on the amount of cAMP present, PKA utilizes a phosphate from ATP to phosphorylate a receptive substrate, thereby causing the concentration of ATP to decrease in a sample, thereby causing a decrease in luminescence, or light output. As such, as cAMP concentration in a sample increases a reciprocal decrease in luminescence is seen which is correlated to the amount of cAMP, adenylyl cyclase, and/or GPCR activity present in the initial sample.

In one embodiment, the present invention provides a method for determining the amount of cyclic nucleotides in a sample comprising a sample with may contain a cyclic nucleotide, adding to said sample an inactive enzyme capable of being activated by said cyclic nucleotide, adding a detection system capable of detecting the activity of said activated enzyme and generating a detectable signal, and determining the amount of cyclic nucleotide present in said sample based on said signal. In some embodiments, said sample comprises a lysate. In some embodiments, the sample lysate is derived from bacteria, yeast or mammalian cells. In some embodiments, said sample comprises plasma membranes, cellular membranes, and/or organellar membranes. In some embodiments, said cyclic nucleotide is cAMP or cGMP. In some embodiments, said inactive enzyme is a cAMP dependent protein kinase or a cGMP dependent protein kinase. In some embodiments, said detection system comprises a substrate capable of being phosphorylated by PKA or PKG. In some embodiments, said substrate comprises SEQ ID NO: 1. In some embodiments, said detection system further comprises an enzyme capable of utilizing ATP to generate a luminescent signal wherein said enzyme is luciferase. In some embodiments, said substrate comprises a radioactively labeled biotinylated substrate further comprising SEQ ID NO: 1. In some embodiments, said detection system further comprises a streptavidin coated binding surface. In some embodiments, said substrate comprises a fluorescently labeled substrate further comprising SEQ ID NO: 1, wherein said fluorescent label is preferentially rhodamine. In some embodiments, the method of the present invention further comprises the addition of one or more inhibitors of phosphodiesterases, and/or the addition of an agonist or antagonist capable of affecting cyclic nucleotide amounts in said sample. In some embodiments, said agonist or antagonist modulates adenylyl cyclase activity and/or GPCR activity and/or PDE activity.

In one embodiment, the present invention provides a method for determining adenylyl cyclase activity in a sample comprising a sample that may contain adenylyl cyclase, adding to said sample an inactive enzyme capable of being activated by cAMP, adding a detection system capable of detecting the activity of said activated enzyme and generating a detectable signal, and determining adenylyl cyclase activity present in said sample based on said signal. In some embodiments, said sample comprises a lysate. In some embodiments, the sample lysate is derived from bacteria, yeast or mammalian cells. In some embodiments, said sample comprises plasma membranes, cellular membranes, and/or organellar membranes. In some embodiments, said inactive enzyme is a cAMP dependent protein kinase. In some embodiments, said detection system comprises a substrate capable of being phosphorylated by PKA. In some embodiments, said substrate comprises SEQ ID NO: 1. In some embodiments, said detection system further comprises an enzyme capable of utilizing ATP to generate a luminescent signal wherein said enzyme is luciferase. In some embodiments, said substrate comprises a radioactively labeled biotinylated substrate further comprising SEQ ID NO: 1. In some embodiments, said detection system further comprises a streptavidin coated binding surface. In some embodiments, said substrate comprises a fluorescently labeled substrate further comprising SEQ ID NO: 1, wherein said fluorescent label is preferentially rhodamine. In some embodiments, the method of the present invention further comprises the addition of one or more inhibitors of phosphodiesterases, and/or the addition of an agonist or antagonist capable of affecting adenylyl cyclase activity.

In one embodiment, the present invention provides a method for determining phosphodiesterase activity in a sample comprising a sample that may contain a phosphodiesterase, adding to said sample an inactive enzyme capable of being activated by cAMP, adding a detection system capable of detecting the activity of said activated enzyme and generating a detectable signal, and determining phosphodiesterase activity present in said sample based on said signal. In some embodiments, said sample comprises a lysate. In some embodiments, the sample lysate is derived from bacteria, yeast or mammalian cells. In some embodiments, said sample comprises plasma membranes, cellular membranes, and/or organellar membranes. In some embodiments, said phosphodiesterase is a cyclic nucleotide phosphodiesterase. In some embodiments, said cyclic nucleotide is cAMP or cGMP. In some embodiments, said inactive enzyme is a cAMP dependent protein kinase or a cGMP dependent protein kinase. In some embodiments, said detection system comprises a substrate capable of being phosphorylated by PKA or PKG. In some embodiments, said substrate comprises SEQ ID NO: 1. In some embodiments, said detection system further comprises an enzyme capable of utilizing ATP to generate a luminescent signal wherein said enzyme is luciferase. In some embodiments, said substrate comprises a radioactively labeled biotinylated substrate further comprising SEQ ID NO: 1. In some embodiments, said detection system further comprises a streptavidin coated binding surface. In some embodiments, said substrate comprises a fluorescently labeled substrate further comprising SEQ ID NO: 1, wherein said fluorescent label is preferentially rhodamine. In some embodiments, the method of the present invention further comprises the addition of one or more inhibitors of phosphodiesterase activity.

In one embodiment, the present invention provides a method for determining G-protein coupled receptor activity in a sample comprising a sample that may contain a GPCR, adding to said sample an inactive enzyme capable of being activated by cAMP, adding a detection system capable of detecting the activity of said activated enzyme and generating a detectable signal, and determining GPCR activity present in said sample based on said signal. In some embodiments, said sample comprises a lysate, more preferably a lysate derived from mammalian cells. In some embodiments, said sample comprises plasma membranes. In some embodiments, said inactive enzyme is a cAMP dependent protein kinase. In some embodiments, said detection system comprises a substrate capable of being phosphorylated by PKA. In some embodiments, said substrate comprises SEQ ID NO: 1. In some embodiments, said detection system further comprises an enzyme capable of utilizing ATP to generate a luminescent signal wherein said enzyme is luciferase. In some embodiments, said substrate comprises a radioactively labeled biotinylated substrate further comprising SEQ ID NO: 1. In some embodiments, said detection system further comprises a streptavidin coated binding surface. In some embodiments, said substrate comprises a fluorescently labeled substrate further comprising SEQ ID NO: 1, wherein said fluorescent label is preferentially rhodamine. In some embodiments, the method of the present invention further comprises the addition of one or more inhibitors of phosphodiesterase activity and/or addition of an agonist or antagonist of GPCRs.

In one embodiment, the present invention provides a kit for determining the concentration of cyclic nucleotides in a sample comprising a cyclic nucleotide, a protein kinase, ATP, a protein kinase substrate, and instructions for using said kit in determining said concentration of said protein kinase substrate. In some embodiments, said kit further comprises a luminescent detection system. In some embodiments, said kit further comprises a fluorescent detection system. In some embodiments, said kit further comprises a radioactive detection system.

In one embodiment, the present invention provides a kit for determining the cyclic nucleotide phosphodiesterase activity in a sample comprising substrates from cAMP and cGMP, a protein kinase, a protein kinase substrate, and instructions for using said kit in determining said activity of said cyclic nucleotide phosphodiesterase. In some embodiments, said kit further comprises a luminescent detection system. In some embodiments, said kit further comprises a fluorescent detection system. In some embodiments, said kit further comprises a radioactive detection system.

DEFINITIONS

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, cell lysates, and components of cell lysates. Environmental samples include environmental material such as surface matter, soil, water, crystals and industrial samples. A sample may or may not contain a substance that modulates cyclic nucleotide concentration. Such examples are not however to be construed as limiting the sample types applicable to the present invention.

As used herein, the term "agonist" refers to any substance that may stimulate the activity of a receptor, enzyme, or other protein.

As used herein, the term "antagonist" refers to any substance that may inhibit the activity of a receptor, enzyme, or other protein.

As used herein, the term "substrate" refers to any polypeptide that is acted on by an enzyme or other protein.

As used herein, the term "inhibitor" refers to any compound that inhibits enzyme activity or biochemical reactions.

As used herein, the term "detection" refers to qualitatively or quantitatively determining the presence or absence of a substance within a sample. For example, methods of detection as described herein include, but are not limited to, luminescence, radioactivity and fluorescence.

As used herein, the term "lysate" refers, in its broadest sense, to the cellular debris and fluid that is released from a cell when the cell membrane is broken apart, or lysed. For example, as described herein lysates that find utility in the present invention include, but are not limited to, lysates from prokaryotic cells such as bacteria, and lysates from eukaryotic cells such as yeast, plant and mammalian cell lysates. Cellular debris that is a product of eukaryotic cellular lysis includes, but is not limited to, organelles (e.g., endoplasmic reticulum, nucleus, ribosomes, mitochondria, etc), cellular structural components such as microtubules, plasma membranes, organellar membranes, cellular membranes, and the like.

DETAILED DESCRIPTION OF THE INVENTION

Figure 1:
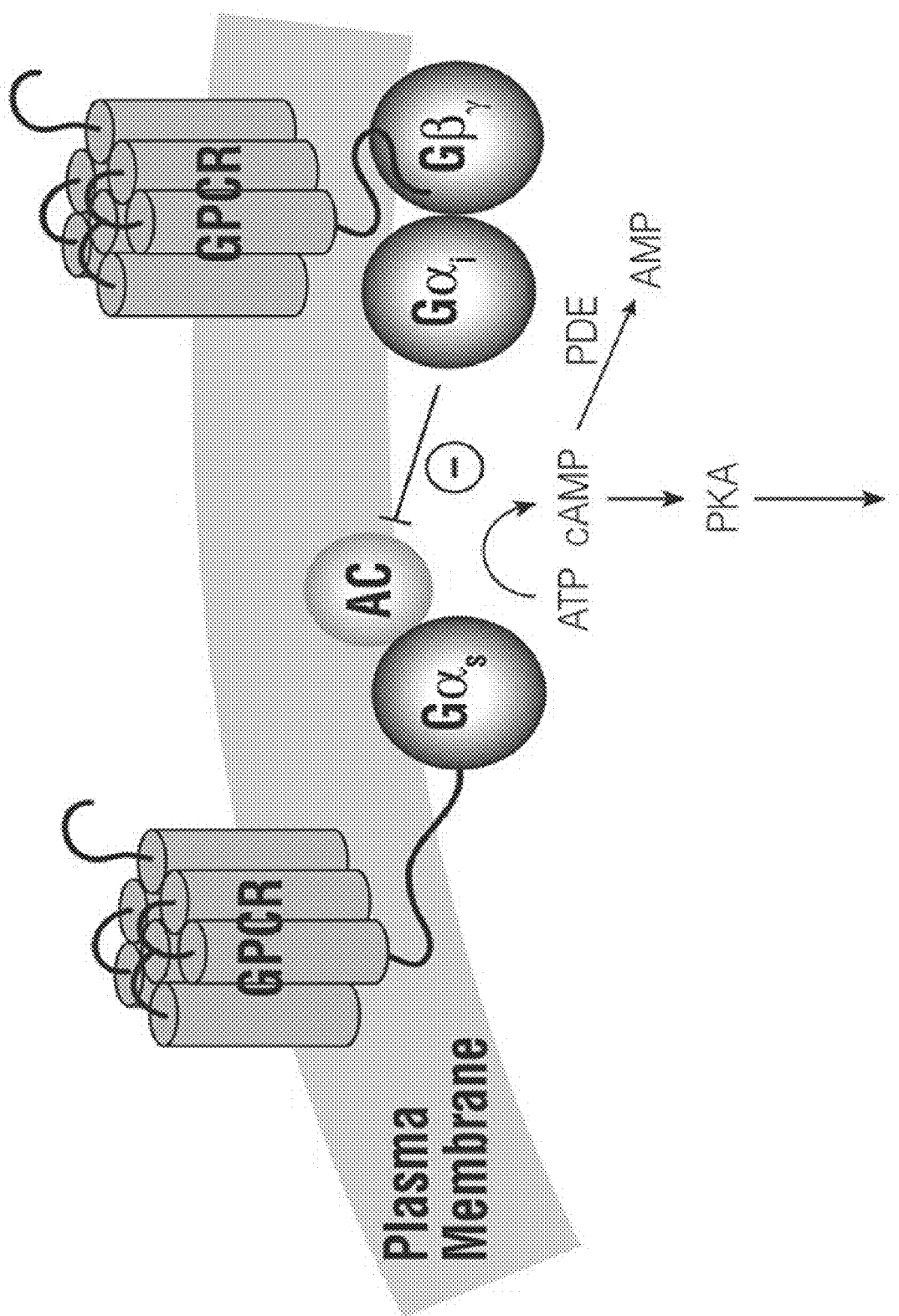
FIG. 1 shows a G-protein coupled receptor signaling pathway. A G-protein coupled receptor subunit $G_{\alpha s}$ stimulates adenylyl cyclase and cAMP is generated from ATP. Cyclic AMP binds to the regulatory subunit of PKA releasing the catalytic subunits that phosphorylate substrates of PKA. Conversely, an inhibitory GPCR subunit $G_{\alpha i}$ inhibits adenylyl cyclase thereby blocking phosphorylation of PKA substrates. Phosphodiesterases affect PKA substrate phosphorylation by hydrolyzing cAMP to AMP and cGMP to GMP, which does not bind to the PKA regulatory subunits.

In one embodiment, the methods of the present invention provide for monitoring the modulations of cellular proteins by monitoring the changes in activity of a protein kinase due to activation by cyclic nucleotides. Cellular levels of cyclic nucleotides reflect the balance between the activities of cyclases and cyclic nucleotide phosphodiesterases (FIG. 1). Cyclic AMP binds to the regulatory subunits of the tetramer PKA. Cyclic GMP binds to the regulatory subunit of cGMP dependent protein kinase, or PKG. The present invention is not limited to a particular mechanism. Indeed, an understanding of the mechanism is not necessary to practice the present invention. Nonetheless, it was found that not only does cAMP bind to the regulatory subunits of type II PKA, but cGMP also binds to type H PKA regulatory subunits. Therefore, once cAMP or cGMP binds to the regulatory subunits of PKA, the PKA active catalytic subunits are capable of phosphorylating serine/threonine protein kinase substrates by transfer of a phosphate from ATP to the substrate phosphorylation site. As such, PKA activity serves as an indicator of the amount of cAMP or cGMP present in a sample.

As previously stated, cyclases and phosphodiesterases directly influence the amount of cyclic nucleotides present in a sample. For example, when activators or inhibitors of adenylyl cyclase are present, cAMP concentration will increase or decrease, respectively, thereby causing an increase or decrease in PKA activity. The same is found for activators or inhibitors of guanylyl cyclase. Adenylyl cyclase is part of a signaling pathway associated with GPCRs. An agonist or antagonist of a GPCR will affect the activity of adenylyl cyclase, and thus PKA activity. Conversely, phosphodiesterases hydrolyze cAMP to AMP and cGMP to GMP, so as agonists or antagonists of this enzyme are present in a sample, cyclic nucleotide concentration will decrease or increase, respectively, thereby causing a decrease or increase in PKA activity. As such, the methods as described herein provide for monitoring modulations of cAMP, adenylyl cyclase, cGMP, phosphodiesterases, and GPCRs.

To maximize the event that only cyclic nucleotides in a sample are able to activate the PKA of the method, the PKA of the method should be as pure of a PKA type H holoenzyme (e.g., PKA regulatory and catalytic subunits are associated) as possible. Preferably, the PKA type II holoenzyme is substantially free from unassociated active catalytic subunits. The purity of the PKA holo-enzyme should be sufficient to permit monitoring of the modulation of the cyclases and GPCRs when compared to a control. Similarly, if PKG is used as described herein, it should be similarly substantially free from unassociated active catalytic subunits. To maximize the methods as described herein, the PKA holo-enzyme used for said methods should contain <10% (>90% pure), preferably <5% (>95% pure), more preferably <1% (>99% pure), and most preferably <0.1% (>99.9% pure) unassociated active catalytic subunits. Assays to test for the percentage of unassociated active catalytic subunits are those that, for example, compare the activity of a test sample of PKA holo-enzyme with that of a control sample that contains inactivated holo-enzyme.

One embodiment of the present invention provides for determining the concentration of cyclic nucleotides in a sample. In some embodiments, the present method may be used to determine the amount of cAMP or cGMP in a sample. A sample of the present method comprises, but is not limited to, cell culture media, a buffered solution, cells, and cell lysates. In some embodiments, said sample comprises a lysate. In some embodiments, the sample lysate is derived from bacteria, yeast or mammalian cells. In some embodiments, said sample comprises plasma membranes, cellular membranes, and/or organellar membranes.

In one embodiment, to determine the concentration of cyclic nucleotides in a sample, the present invention comprises a protein kinase, substrate and ATP. In some embodiments, the present invention comprises PKA or PKG, such that as a cyclic nucleotide binds to the regulatory subunits of the kinase the active catalytic subunits are capable of utilizing ATP in phosphorylating a substrate. In some embodiments, the invention comprises a serine/threonine protein kinase substrate that demonstrates an increased affinity for PKA or PKG. In some embodiments, the method comprises a substrate comprising the polypeptide sequence LRRASLG (SEQ ID NO: 1).

Detection methods used to determine the cAMP concentration of a sample using the present method includes, but is not limited to, the use of bioluminescence, chemiluminescence, colorimetry, radioactivity, or differential output based on different fluorescence technologies. In one embodiment, kinase activity is measured in the methods described herein and any suitable kinase assay can be used. For example, known kinase assays include, but are not limited to, luminescent assays such as Kinase-Glo™ Luminescent Kinase Assay (Promega Corporation, Madison Wis.) and PKLight™ HTS Protein Kinase Assay (Cambrex, N.J.), fluorescent assays such as Kinome™ Hunter (DiscoverX, Fremont Calif.) and HitHunter™ FP Kinase Assay (DiscoverX, Fremont Calif.) and ProFluor™ PKA Assay (Promega Corporation, Madison Wis.), and radioactivity assays such as SignaTECT® cAMP-Dependent Protein Kinase (PKA) Assay System (Promega Corporation, Madison Wis.).

It is contemplated that different luminescent detection methods exhibit different patterns of luminescent output with respect to PKA activity. In one embodiment, a luminescent detection method is a method that detects kinase activity. In some embodiments, a luminescent detection method as described herein comprises an enzyme, a substrate, and an appropriate buffer. In some embodiments, the present invention detects changes in cAMP concentration by bioluminescence. In some embodiments, the present invention detects changes in cAMP concentration by utilizing a luciferase. In some embodiments, the present invention detects changes in cAMP concentration by utilizing a coleopteran luciferase. For example, as cyclic nucleotides bind to the regulatory subunits of PKA the catalytic subunits are able to utilize ATP for substrate phosphorylation and ATP is depleted. The coleopteran luciferase enzyme utilizes ATP and other co-factors to convert its cognate substrate luciferin into oxyluciferin, a byproduct of the reaction being luminescence, or light. As ATP decreases in a sample there is less available for luciferase and a decrease in luminescence is seen. The luminescent ouput (relative light units or RLUs) is used to detect a change in luminescence of a sample relative to that of a control. Other luminescent detection methods may exhibit differential light output with respect to PKA activity.

In one embodiment, the present invention provides a detection system whereby cyclic nucleotide concentration in a sample is determined by radioactive means. Different radioactive detection methods may exhibit different patterns of radioactive output with respect to PKA activity. In some embodiments, a radioactive detection method is a method to detect kinase activity. In some embodiments, the radioactive detection method as described herein comprises a modified substrate, a suitable buffer, and a surface capable of capturing the modified substrate. In some embodiments, the radioactive method comprises the SignaTECT® cAMP-Dependent Protein Kinase (PKA) Assay System (Promega Corporation, Madison, Wis.). In some embodiments, the radioactive detection method comprises radioactive ATP. In some embodiments, the radioactive detection method comprises $\gamma^{32}$P-ATP or $\gamma^{33}$P-ATP.

In one embodiment, the radioactive detection method further comprises a substrate capable of being phosphorylated by PKA. In some embodiments, the radioactive detection method comprises a substrate capable of being phosphorylated by PKA in association with a ligand. In some embodiments, the radioactive detection method comprises a biotinylated substrate comprising the polypeptide sequence LRRASLG (SEQ ID NO: 1). In some embodiments, the detection method as described herein further comprises a surface upon which resides a compound that captures the substrate/ligand. For example, the surface is a membrane that is coated with streptavidin. As the cyclic nucleotides bind to the regulatory subunit of PKA, the catalytic subunits utilize the radioactively labeled ATP and transfer a radioactive phosphate onto the substrate thereby causing the substrate to be radioactive. The radioactive ligand-coupled substrate is captured on a surface upon which resides a compound that will capture the ligand (e.g. strepravidin). In some embodiments, the surface is washed free of excess radioactivity, and radioactivity captured on the capture surface is measured. The radioactive output (counts per unit time) is used to detect a change in radioactivity of a sample relative to that of a control.

In one embodiment, the present invention provides a detection system whereby cyclic nucleotide concentration in a sample is determined by fluorescent means. Different fluorescence detection methods may exhibit different patterns of fluorescence output with respect to PKA activity. In one embodiment, a fluorescence detection method is a method to detect kinase activity. In some embodiments, the fluorescent detection method of the present method comprises an enzyme, a modified substrate, and a suitable buffer. In some embodiments, the fluorescent method comprises the ProFluor™ PKA Assay (Promega Corporation, Madison, Wis.). In one embodiment, the fluorescent detection method of the present invention comprises a fluorophore. In some embodiments, the fluorescent detection method comprises the fluorophore rhodamine-110.

In one embodiment, the fluorescent detection method as described herein further comprises a substrate. In some embodiments, the substrate of the fluorescent detection method comprises the polypeptide sequence LRRASLG (SEQ ID NO: 1). In some embodiments, the fluorescent detection method comprises an enzyme. In some embodiments, an enzyme of the fluorescent detection method as described herein is a protease. In some embodiments, the protease of the fluorescent detection method is capable of digesting the substrate when it is not phosphorylated.

In one embodiment, the fluorescent detection method comprises a substrate in association with a fluorophore. In some embodiments, the fluorescent detection method comprises two substrates in association with a fluorophore such that as the fluorophore is in association with the substrates there in decreased fluorescence when compared to a fluorophore that is free from association with the substrate. For example, as the cyclic nucleotides bind to the regulatory subunits of PKA the catalytic subunits are capable of phosphorylating a cognate substrate. The substrates of the fluorescent detection method are coupled to a fluorophore such that the fluorophore exhibits decreased fluorescence when bound to the substrates. A protease as described herein digests the substrate up to the point of phosphorylation. Therefore, if cyclic nucleotide concentration in a sample is increased, more substrate will be phosphorylated and the fluorescence will remain low. Conversely, if cyclic nucleotide concentration in a sample is low, then less substrate will be phosphorylated, protease digestion of the non-phosphorylated substrate will be complete thereby releasing the fluorophore and fluorescence will increase. The fluorescence output (relative fluorescent units) is detected and a change in fluorescence of a sample relative to that of a control is determined.

In one embodiment, the present invention provides for determining cyclic nucleotide concentration in a sample and correlating the cyclic nucleotide concentration with cyclase activity in a sample. In one embodiment, the cyclic nucleotides to be detected are cAMP or cGMP. A sample of the present method comprises, but is not limited to, cell culture media, a buffered solution, cells, and cell lysates. In some embodiments, said sample comprises a lysate. In some embodiments, the sample lysate is derived from bacteria, yeast or mammalian cells. In some embodiments, said sample comprises plasma membranes, cellular membranes, and/or organellar membranes. In some embodiments, the cyclase of the present invention is chosen from a group consisting of adenylyl cyclase and guanylyl cyclase. In one embodiment, the cyclase of the present invention is adenylyl cyclase. In some embodiments, the present invention is used to find substances that have an affect on adenylyl cyclase activity. For example, methods of the present invention are used to find substances that either stimulate (e.g. increase) or inhibit (e.g. decrease) adenylyl cyclase activity. Examples of substances that stimulate adenylyl cyclase activity include, but are not limited to, forskolin and forskolin derivatives such as 7-Deacetyl-forskolin, 6-Acetyl-7-deacetyl-forskolin and 7-Deacetyl-7-O-hemisuccinyl-forskolin. Examples of substances that inhibit adenylyl cyclase activity include, but are not limited to; cell permeable inhibitors such as 9-(Tetrahydrofuryl)-adenine, 2',5'-Dideoxyadenosine and 9-(Cyclopentyl)-adenine; competitive inhibitors such as substrate analogs β-L-2',3'-Dideoxy-adenosine-5'-triphosphate, β-L-Adenosine 5'-triphosphate and Adenosine 5'-(βγ-methylene)-triphosphate; non-competitive inhibitors such as 9-(Arabinofuranosyl)-adenine, 9-(Xylofuranosyl)-adenine and 2',5'-Dideoxyadenosine 3'-tetraphosphate; other inhibitors such as Cis-N-(2-Phenylcyclopentyl)azacyclotridec-1-en-2-amine, 9-(2-Diphosphorylphosphonylmethoxyethyl) adenine and polyadenylyl.

In one embodiment, to determine the affect of substances on adenylyl cyclase activity, the methods of the present invention comprise a protein kinase, substrate and ATP. In some embodiments, the present method comprises a cAMP dependent protein kinase (PKA) such that as a cyclic nucleotide binds to the regulatory subunits of the kinase and releases the active catalytic subunits that are capable of utilizing ATP in phosphorylating a serine/threonine protein kinase substrate. In some embodiments, the present method comprises a serine/threonine protein kinase substrate that demonstrates an increased affinity for the free catalytic subunit of PKA. In some embodiments, the present method comprises a substrate comprising the polypeptide sequence LRRASLG (SEQ ID NO: 1). Adenylyl cyclase generates cAMP from ATP, therefore a substance which affects adenylyl cyclase activity impacts the concentration of cAMP in a sample. Detection methods have been described in previous embodiments, and those detection methods are equally applicable here. For example, as substances affect the activity of adenylyl cyclase in a sample, the cAMP concentration will increase or decrease, which will cause an increase or decrease in substrate phosphorylation via PKA. The detection method output as previously described is used to determine the increase or decrease in cAMP concentration that is correlated with an increase or decrease in adenylyl cyclase activity of a sample relative to that of a control. Therefore, when an agonist of an adenylyl cyclase is present in a sample thereby stimulating adenylyl cyclase activity, there is an increase in cAMP production that is reflected in the output of the detection method of use. Conversely, if an antagonist of an adenylyl cyclase is present in a sample thereby inhibiting adenylyl cyclase activity, there is a decrease in cAMP production, which is reflected in the output of the detection method of use.

In one embodiment, the present invention determines the concentration of cyclic nucleotides in a sample and correlates the cyclic nucleotide concentration with phosphodiesterase activity. In some embodiments, the cyclic nucleotides to be detected are cAMP or cGMP. In some embodiments, if cGMP is the cyclic nucleotide used for detection, then the sample has an overabundance of cGMP relative to cAMP. In some embodiments, when cGMP is the cyclic nucleotide used for detection, phosphodiesterase IV (a cAMP specific phosphodiesterase) is present in the sample. In some embodiments, a sample of the present invention includes, but is not limited to, cell culture media, a buffered solution, cells, and cell lysates. In some embodiments, said sample comprises a lysate. In some embodiments, the sample lysate is derived from bacteria, yeast or mammalian cells. In some embodiments, said sample comprises plasma membranes, cellular membranes, and/or organellar membranes.

In one embodiment, the phosphodiesterase is a cyclic nucleotide phosphodiesterase. In some embodiments, the cyclic nucleotide phosphodiesterase activity to be determined, when detecting cAMP activation of PKA, is from a group consisting of phosphodiesterase II, phosphodiesterase III, and phosphodiesterase IV. In some embodiments, the cyclic nucleotide phosphodiesterase activity to be determined, when detecting cGMP activation of PKA, is from a group consisting of phosphodiesterase II, phosphodiesterase III, and phosphodiesterase IV and phosphodiesterase V. In some embodiments, methods of the present invention are used to find substances that have an affect on phosphodiesterase activity. In some embodiments, the present invention is used to find substances that either stimulate (e.g. increase) or inhibit (e.g. decrease) phosphodiesterase activity. An examples of a substance that inhibits phosphodiesterase II activity includes, but is not limited to, Erythro-9-(2-hydroxy-3-nonyl)adenine. Examples of substances that inhibit phosphodiesterase III activity include, but are not limited to, 1,6-Dihydro-2-methyl-6-oxo-(3,4'-bipyridine)-5-carbonitrile, 1,3-Dihydro-4-methyl-5-(4-methylthiobenzoyl)-2H-imidazol-2-one and Trequisin hydrochloride. Examples of substances that inhibit phosphodiesterase IV activity include, but are not limited to, 4-[3-(Cyclopentyloxy)-4-methoxyphenyl]-2-pyrrolidinone, 4-(3-Butoxy-4-methoxybenzyl)imidazolidin-2-one and 1-Ethyl-4-[91-methylethylidene-hydrazino]1H-pyrazolo[3,4-b]pyridine-5-carboxylic acid ethyl ester hydrochloride. Examples of substances that inhibit phosphodiesterase V activity include, but are not limited to, 1,4-Dihydro-5-(2-propoxyphenyl)-7H-1,2,3-triazolo(4,5-d-pyrimidin-7-one (Zaprinist), Dipyridamole and 1-[4-ethoxy-3-(6,7-dihydro-1-methyl-7-oxo-3-propyl-1H-pyrazolo[4,3-d]pyrimidin-5-yl-phenylsulfolyl]-4-methylpiperazine citrate. An example of a substance that is a non-selective inhibitor of cyclic nucleotide phosphodiesterases is 3-Isobutyl-1-methylxanthine.

In one embodiment, to determine the affect of substances on phosphodiesterase activity, the present invention comprises cyclic nucleotides, a protein kinase, a substrate and ATP. In some embodiments, the present invention comprises PKA such that as a cyclic nucleotide, either cAMP or cGMP, binds to the regulatory subunits of the kinase are released and become capable of utilizing ATP in phosphorylating a serine/threonine protein kinase substrate. In some embodiments, the present invention comprises a serine/threonine protein kinase substrate that demonstrates an increased affinity for a cAMP dependent protein kinase. In some embodiments, the present invention comprises a substrate comprising the polypeptide sequence LRRASLG (SEQ ID NO: 1).

Phosphodiesterases hydrolyze cyclic nucleotides, cAMP to AMP and cGMP to GMP. Detection methods have been described in previous embodiments, and those detection methods are equally applicable here. For example, as substances modulate the activity of a phosphodiesterase in a sample, the cyclic nucleotide concentration increases or decreases, thereby causing an increase or decrease in substrate phosphorylation via PKA. A detection method output as described herein is used to determine the increase or decrease in cyclic nucleotide concentration that is correlated with an decrease or increase in phosphodiesterase activity of a sample relative to that of a control. Therefore, when an agonist of a phosphodiesterase is present in a sample thereby stimulating phosphodiesterase activity, there is an increase in hydrolysis of cAMP to AMP or cGMP to GMP, which is reflected in the output of the detection method of use. Conversely, if an antagonist of a phosphodiesterase is present in a sample thereby inhibiting phosphodiesterase activity, there is a decrease in hydrolysis of cAMP to AMP or cGMP to GMP, which is reflected in the output of the detection method of use.

In one embodiment, a method as described herein determines the concentration of cyclic nucleotides in a sample and correlates the cyclic nucleotide concentration with G-protein coupled receptor (GPCR) activity. In some embodiments, the cyclic nucleotides to be detected are cAMP or cGMP. In some embodiments, a sample of the present invention comprises, but is not limited to, cell culture media, a buffered solution, cells, and cell lysates. In some embodiments, said sample comprises a lysate. In some embodiments, the sample lysate is derived from bacteria, yeast or mammalian cells. In some embodiments, said sample comprises plasma membranes, cellular membranes, and/or organellar membranes. In some embodiments, methods of the present invention are used to find substances that have an affect on GPCR activity. In some embodiments, the present invention is used to find substances that either stimulate (e.g. increase) or inhibit (e.g. decrease) GPCR activity. A representative list of G-protein coupled receptors can be found in Hermans, E., 2003, Pharmacology & Therapeutics 99:25-44, incorporated herein by reference in its entirety. Examples of GPCR include, but are not limited to, the dopamine receptor D1 (SEQ ID NO: 2) (U.S. Pat. No. 5,389,543) and the β-2-adrenergic receptor and the prostaglandin E1 receptor. Examples of substances that increase dopamine receptor D1 (SEQ ID NO: 2) activity include, but are not limited to, dopamine, apomorphine, 1-Phenyl-2,3,4, 5-tetrahydro-(1H)-3-benzazepine-7,8-diol (SKF 38393) and 6-Chloro-7,8-dihydroxy-3-allyl-1-phenyl-2,3,4,5-tetra-hydro-1H-3-benzazepine hydrobromide (SKF 82958). Other dopamine receptors include, but are not limited to, D2, D3, D4, and D5 receptors. An example of a substance that increases the activity of the β-2-adrenergic receptor includes, but is not limited to, isoproterenol. An example of a substance that increases activity of the prostaglandin E2 receptor includes, but is not limited, CP-533,536. Other prostaglandin receptors includes, but are not limited to, EP1, EP3 and EP4.

In one embodiment, to determine the affect of substances on GPCR activity, methods of the present invention comprise cyclic nucleotides, a protein kinase, a substrate and ATP. In some embodiments, the present invention comprises PKA such that as a cyclic nucleotide binds to the regulatory subunits of the kinase and active catalytic subunits are capable of utilizing ATP in phosphorylating a serine/threonine protein kinase substrate. In some embodiments, the present invention comprises a PKA which upon binding of cyclic nucleotides to its subunits, the kinase activity of the catalytic subunit is generated and utilizes ATP for phosphorylating a serine/threonine protein kinase substrate. In some embodiments, the present invention comprises PKA, which upon binding of cyclic nucleotides to its regulatory subunit, the kinase activity of the catalytic subunits is generated and utilizes ATP for phosphorylating a serine/threonine protein kinase substrate. In some embodiments, the substrate comprises the polypeptide sequence LRRASLG (SEQ ID NO: 1).

G-protein coupled receptors are integral membrane proteins which are involved in signaling from outside to inside a cell. There are many diseases that are caused by GPCR malfunction, therefore the ability of methods of the present invention to define whether substances have an affect on GPCR activity is of importance both academically and clinically. As substances either stimulate or inhibit a G-protein coupled receptor, the associated adenylyl cyclase is affected wherein its activity will increase or decrease, respectively. As the adenylyl cyclase activity is modulated by stimulation or inhibition through the GPCR, the amount of ATP that is converted to cAMP is affected, thereby controlling the amount of cAMP that is available to associate with the regulatory subunits of PKA, which in turn controls the amount of substrate phosphorylation that occurs in a sample.

Detection methods have been described in previous embodiments, and those detection methods are equally applicable here. As substances affect the activity of a GPCR in a sample, the cyclic nucleotide concentration changes accordingly, which causes an increase or decrease in substrate phosphorylation via PKA. The detection method output is used to determine the increase or decrease in cAMP concentration that is correlated to an increase or decrease in GPCR activity of a sample relative to that of a control. Therefore, when an agonist of a GPCR that is coupled to $G\alpha_s$ is present in a sample, adenylyl cyclase activity is stimulated causing an increase in cAMP generation, which is reflected in the output of the detection method used.

Conversely, if an antagonist of a GPCR that is coupled to $G\alpha_s$ is present in a sample, adenylyl cyclase activity is inhibited and there is a decrease in cAMP generation that is reflected in the output of the detection method used. When an agonist of GPCR coupled to $G\alpha_i$ is present in a sample, adenylyl cyclase activity is inhibited causing a decrease in cAMP generation that is reflected in the output of the detection method used. When an antagonist of GPCR coupled to $G\alpha_i$ is present in a sample, adenylyl cyclase activity is not inhibited, therefore a potential increase in cAMP generation is realized and is reflected in the output of the detection method used.

In one embodiment, the present invention provides a kit comprising one or more reagents for conducting any method as described herein. In some embodiments, said reagents are sufficient for conducting the methods as described herein. In some embodiments, said kit reagents include, but are not limited to, controls, instructions, buffers, software for data analysis, equipment for practicing the detection methods as described herein, one or more containers comprising one or more reagents for practicing the methods as described herein, and tissue culture cells. In some embodiments, said kits comprise cyclic nucleotides, such as cAMP or cGMP. In some embodiments, said kits comprise enzymes such as PKA and PKG. In some embodiments, said kits comprise cell lysis buffers or solutions. In some embodiments, said kits comprise reaction buffers. In some embodiments, said kits comprise protein kinase substrates, either lyophilized or in solution. In some embodiments, said kits contain buffers and reagents amenable to a particular detection system or method, for example, luminescence, fluorescence, or radioactive detection systems.

The terminology employed herein is for the purpose of description and should not be regarded as limiting. Further, the embodiments as described herein are exemplary of what is practiced by using the present kits, methods and compositions. They are not intended to be limiting, and any person skilled in the art would appreciate the equivalents embodied therein.

EXAMPLES

The following examples are provided in order to demonstrate and further illustrate certain preferred embodiments and aspects of the present invention and are not to be construed as limiting the scope thereof.

Example 1—Culture of Mammalian Cells

Mammalian cells HEK D293 (human embryonic kidney) were cultured in the following manner for all cell culture related experiments, unless otherwise stated. Cells were seeded at a density of 5-10,000 cells/well in a poly-D-lysine coated 96-well white, clear bottom tissue culture plate (BD BioCoat™ Poly-D-Lysine Multiwell™ Plates). Cell culture media consisted of Dulbecco's Modified Eagles Medium (DMEM) supplemented with 10% Fetal Bovine Serum (FBS), 1 U penicillin and 1 mg/ml streptomycin. For the stably expressing dopamine receptor D1 cell line, 500 µg/ml of neomycin was added to the culture media for selection and maintenance purposes. Cells were grown at 37° C./5% $CO_2$ for approximately 24 hours until they were 60-75% confluent at which point transfection, induction, or other cellular manipulations were performed.

Example 2—Determination of cAMP Concentration

This experiment was conducted to demonstrate that the present invention can be used to determine cAMP concentration in a sample, and that the present invention can be used with a variety of detection technologies in determining the cAMP concentration of a sample.

Reactions were performed in a poly-D-lysine coated, white, clear bottom 96 well plate however reactions can also be performed in a 384 well plate by decreasing the amount of added reagents proportionately. Higher density plates, such as 1536 well plates, can also potentially be used by scaling down volume additions accordingly.

A three-fold serial dilution of cAMP starting with 25 µM in 2× Induction Buffer (240 mM NaCl, 7.0 mM KCl, 3.0 mM $CaCl_2$, 2.4 mM $MgSO_4$, 2.4 mM $NaH_2PO_4$, 50 mM $NaHCO_3$, 20 mM glucose, 200 µM 3-Isobutyl-1-methylxanthine (IBMX), 100 µM 4-(3-Butoxy-4-methoxybenzyl) imidazolidin-2-one (RO 201724) was made and 10 µl of each dilution was transferred to separate wells of a 96 well plate. To each cAMP dilution well 10 µl of 2× Induction Buffer and 60 µl of PKA/Substrate Reagent (100 ng/well Holoenzyme-R-II α protein kinase A (BIAFFIN GmbH & Co., Kassel, Germany), 25 µM Kemptide, 1 µM rATP, 20 mM $MgCl_2$) were added. The sample plate was incubated at room temperature for 20 minutes followed by addition of 80 µl of Kinase-Glo™ Reagent (Promega Corporation, Madison Wis.). Luminescence was read 10 minutes after addition of the Kinase-Glo™ Reagent and output was recorded as relative light units (RLU, n=2) and plotted against cAMP concentration using GraphPad Prism® Software Version 4.0 (GraphPad Software, San Diego, Calif.).

Figure 2:
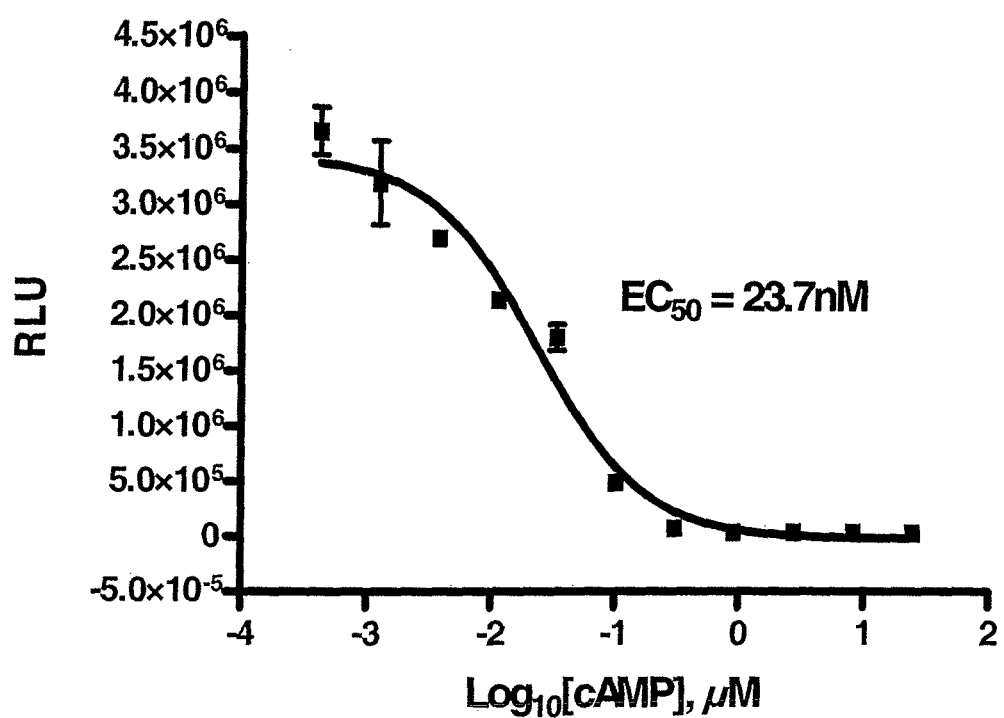
FIG. 2 is a graph showing that as cAMP concentration increases there is a corresponding decrease in sample luminescence in assays comprising PKA.

As can be seen in FIG. 2, as cAMP concentration increases, luminescence decreases. The same reciprocal response was seen when using both the SignaTECT® PKA Assay System (radioactivity counts, Promega Corporation, Madison Wis.) and the ProFluor™ PKA Assay System (relative fluorescence, Promega Corporation, Madison Wis.). Therefore, cAMP concentration can be estimated in an unknown sample using the present invention and the standard curve. Similarly, using this standard curve the concentration of cAMP in cellular extracts of cells that were treated with agonist or antagonist can be estimated.

Example 3—Monitoring Adenylyl Cyclase Activation in the Presence of Forskolin

Reactions were performed in a poly-D-lysine coated, white, clear bottom 96 well plate however reactions can also be performed in a 384 well plate by decreasing the amount of added reagents proportionately. Higher density plates, such as 1536 well plates, can also potentially be used by scaling down volume additions accordingly.

A two-fold serial dilution of 250 µM forskolin in 2× Induction Buffer was made. D293 cells were grown to confluency as described in Example 1. Media was removed from the cultured cells, they were washed three times with Phosphate Buffered Saline (PBS) and 10 µl of each forskolin dilution was added to wells of the 96 well D293 cell culture plate. A control was included by adding 10 µl of 2× Induction Buffer without forskolin to several wells of D293 cells. Cells with and without forskolin were incubated for 15 min. at room temperature, followed by the addition of 10 µl of 2× Lysis Buffer (80 mM Tris-HCl, pH 7.5, 2 mM EDTA, pH 8.0, 2 mM EGTA, pH 7.2, 0.4% Tergitol® NP-9, 20% glycerol, 100 mM NaF, 200 uM $Na_3VO_4$, 400 uM leupeptin, 40 ug/ml aprotinin, 400 uM 1-Chloro-3-tosylamido-7-amino-2-heptanone (TLCK), 400 uM 1-Chloro-3-tosylamido-4-phenyl-2-butanone (TPCK), 200 uM 4-(2-Aminoethyl)benzenesulfonyl fluoride-HCl (ABSF), 200 uM IBMX, and 4 uM rATP (add TPCK last, vortex the buffer prior to adding TPCK to avoid precipitation and keep lysis buffer on ice). Cells were allowed to lyse for 15-30 min. at 4° C., and complete lysis was verified by microscopic evaluation. After lysis, 60 µl of PKA/Substrate Reagent was added to each well and the reactions were incubated for an additional 20 min. at room temperature, followed by the addition of 80 µl of Kinase-Glo™ Reagent. Luminescence was read 10 minutes after addition of the Kinase-Glo™ Reagent and output was recorded as relative light units (RLU, n=2) and plotted against forskolin concentration using GraphPad Prism® Software Version 4.0.

Figure 3:
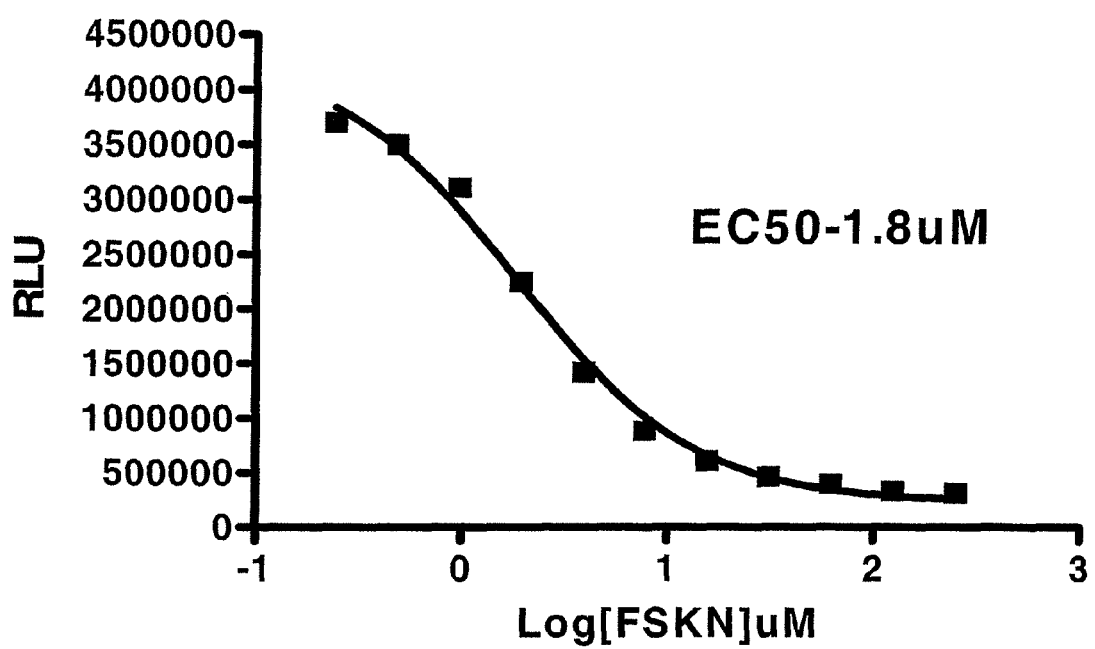
FIG. 3 is a graph showing that as the concentration of forskolin, a direct stimulant of adenylyl cyclase, increases there is a decrease in sample luminescence in assays comprising PKA.

As shown in FIG. 3, as forskolin concentration increases luminescence decreases, thereby demonstrating that the present invention can by used to detect an increase in adenylyl cyclase activity. As forskolin directly stimulates adenylyl cyclase generating cAMP from ATP, cAMP in turn binds to the regulatory subunits of PKA thereby releasing the active PKA catalytic subunits, which in turn uses ATP to phosphorylate the Kemptide substrate. As phosphorylation of Kemptide increases, there is less ATP available to be used by the luciferase enzyme in the Kinase-Glo™ Reagent causing a decrease in luminescence. This effect of forskolin on adenylyl cyclase is seen in FIG. 3 as forskolin concentration increases so does adenylyl cyclase activity that is correlated with a decrease in luminescence. Therefore, the present invention is capable of utilizing cAMP to monitor the induction of adenylyl cyclase by a stimulant.

Example 4—Monitoring Dopamine Receptor D1 Activity in Response to Agonists and Antagonists Experiments were conducted to demonstrate the ability of the present invention to determine the effect of agonists and antagonists on GPCR dopamine receptor D1 (DRD1), a Gα$_s$ coupled receptor, in mammalian cells.

A D293 cell line stably expressing DRD1 was created, using standard molecular biological techniques. Briefly, the gene encoding for DRD1 (Genbank NM000794) was amplified using polymerase chain reaction from a cDNA containing vector (ATCC, HGR213-1) and cloned into the pTarget™ mammalian expression vector following the manufacturer's protocol (Promega Corporation, TM044). The cells were grown as in Example 1 and transfected with pTarget-DRD1 vector 24 hours after seeding. One day post-transfection, the cells were trypsinized and re-plated at various dilutions and fresh media was applied containing 500 µg/ml of the selection drug neomycin. Media was changed every 2-3 days until it was apparent that drug resistant clones were created. Several neomycin resistant clones were selected for further characterization and tested for a dopamine receptor D1 response. The clones that showed the highest response were expanded and frozen stocks created. One of the cloned cell lines was used for subsequent testing.

Three-fold dilutions of 10 µM stock concentrations of the agonists dopamine, SKF 38393, apomorphine, and SKF 82958 were diluted in 2× Induction Buffer. For testing the antagonist SCH 23390, a two-fold serial dilution of the antagonist SCH 23390 (5 uM) was also made in 2× Induction Buffer containing 100 nM of the agonist SKF 38393.

Reactions were performed in a poly-D-lysine coated, white, clear bottom 96 well plate however reactions can also be performed in a 384 well plate by decreasing the amount of added reagents proportionately. Higher density plates, such as 1536 well plates, can also potentially be used by scaling down volume additions accordingly.

Figure 4:
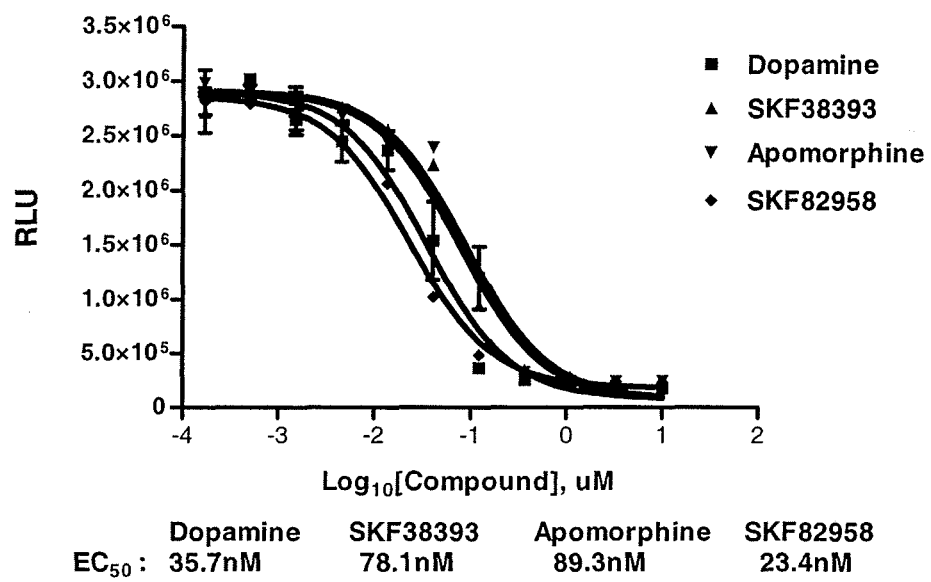
FIG. 4 shows (A) a graph demonstrating that as agonists induce the dopamine receptor D1 ($G_{\alpha s}$-protein coupled receptor) expressed in D293 cells there is a decrease in luminescence in assays comprising PKA and (B) a graph demonstrating that the addition of an antagonist, in the presence of an agonist, to dopamine receptor D1 expressing D293 cells causes an increase in luminescence in assays comprising PKA.
Figure 4:
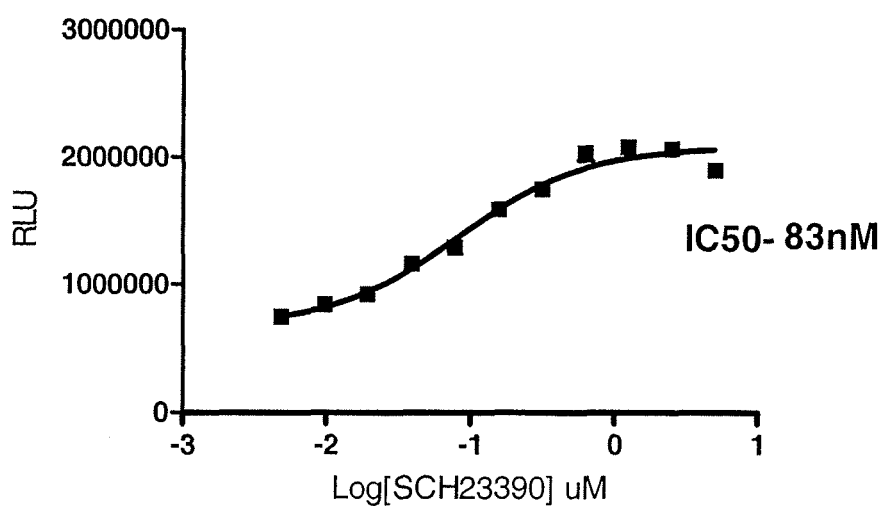

D293 stable cells expressing DRD1 were seeded as described in Example 1. The following day cells were washed 3 times with PBS and 10 µl of each agonist dilution was added to specific wells. For control reactions, 10 µl of 2× Induction Buffer without agonist was used. Induction was allowed to proceed for 30 min. at room temperature, at which point 10 µl of 2× Lysis Buffer was added to each well. Lysis took approximately 20-30 minutes, and complete lysis was verified by microscopic evaluation. Once cells were completely lysed, 60 µl of PKA/Substrate Reagent was added and the reactions were incubated for an additional 20 min. at room temperature. After incubation, 80 µl of Kinase-Glo™ Reagent was added and luminescence read after a 10 min. incubation at room temperature. Output was recorded as RLUs (n=2) and was plotted against agonist concentration using GraphPad Prism® Software Version 4.0. FIG. 4A demonstrates that as agonist concentration increases luminescent signal decreases, thereby showing the inducing effect of each agonist on adenylyl cyclase of DRD1 containing cells. Each agonist has a different effect on DRD1 activity as demonstrated in FIG. 4A by the different EC$_{50}$ values for the various agonists.

For testing the inhibition by an antagonist, D293 stable cells expressing DRD1 were incubated with 10 µl of the antagonist SCH 23390 dilutions in the presence of 100 nM of the agonist SKF 38393, incubated for 30 min. at room temperature. Addition of PKA/Substrate Reagent and Kinase-Glo™ Reagent and subsequent incubations and readings were carried out as described above.

Output was recorded as RLUs (n=2) and was plotted against agonist concentration using GraphPad Prism® Software Version 4.0. FIG. 4B shows that as antagonist concentration increases luminescence increases as well. This increase is due to inhibition of adenylyl cyclase by the antagonistic affect of SCH 23390 to the agonist SKF 38393. Therefore, the present invention finds utility in monitoring the effects of agonists and antagonists on the adenylyl cyclase component of a GPCR coupled to Gα$_s$ pathway.

Example 5—Correlation of cAMP and cGMP with PDE Activity

Experiments were conducted to demonstrate the ability of PKA to monitor changes in cAMP and cGMP concentrations in the presence of cyclic nucleotides and the cognate cyclic nucleotide phosphodiesterases. Experiments were also conducted to monitor the changes of PDE activity in the presence of activators or inhibitors of cyclic nucleotide phosphodiesterases.

Reactions were performed in white 96 well plates however reactions can also be performed in a 384 well plate by decreasing the amount of added reagents proportionately. Higher density plates, such as 1536 well plates, can also potentially be used by scaling down volume additions accordingly.

Figure 5:
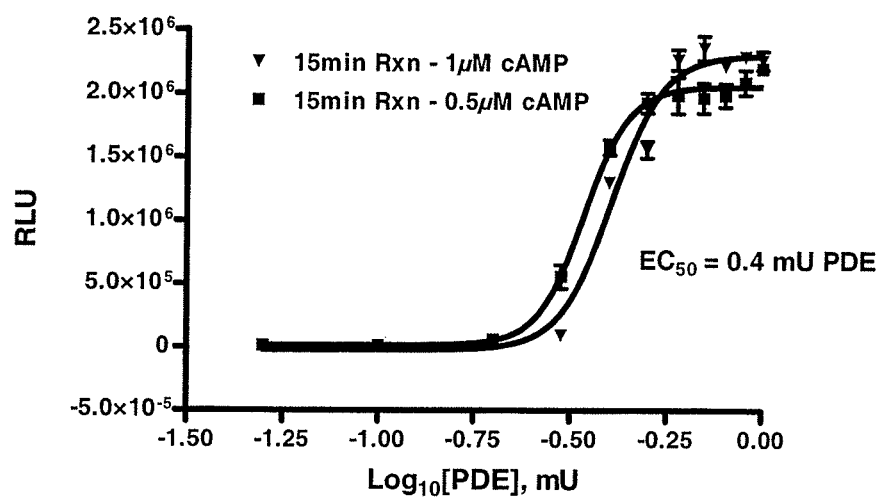
FIG. 5 shows that as phosphodiesterase II concentration increases in the presence of cAMP there is an increase in luminescence in assays comprising PKA, Holoenzyme-R-II α protein kinase A.

A serial dilution of Bovine Brain Phosphodiesterase II (Sigma, PDE II), which hydrolyzes cAMP to AMP, was created by diluting a 1 mU stock by 1/10 increments (1 mU, 0.9 mU, 0.8 mU, etc.) in 2× Induction Buffer minus IBMX and RO 201724. A 12.5 µl aliquot of each dilution was added to 12.5 µl of a solution containing 50 mM Tris HCl, pH 7.5, 10 mM MgCl$_2$, 50 µM CaCl2, 0.1 mg/ml BSA, 20 µM calmodulin (CaM), and 0.5 or 1.0 µM cAMP, total volume of 25 µl in a 96 well white plate. The enzyme reactions were incubated at room temperature for 15 min., and the reaction terminated by addition of 12.5 µl of Stop Buffer (40 mM Tris HCl pH 7.5, 20 mM MgCl$_2$, 0.1 mg/ml BSA, 375 µM IBMX and 4 µM ATP). Following addition of the IBMX solution, 25 µl of PKA/Substrate Reagent was added, reactions were incubated for an additional 20 min, and 50 µl of Kinase-Glo™ Reagent was added. Luminescence was measured 10 min. after addition of the Kinase-Glo™ Reagent and output was recorded as RLUs (n=2) and plotted against PDE concentration using GraphPad Prism® Software Version 4.0. As seen in FIG. 5, luminescence increased with increasing PDE II concentration demonstrating the effect of PDE II on cAMP concentrations. As cAMP is hydrolyzed to AMP by PDE II, cAMP concentration decreases, thereby causing an increase in luminescence.

Figure 6:
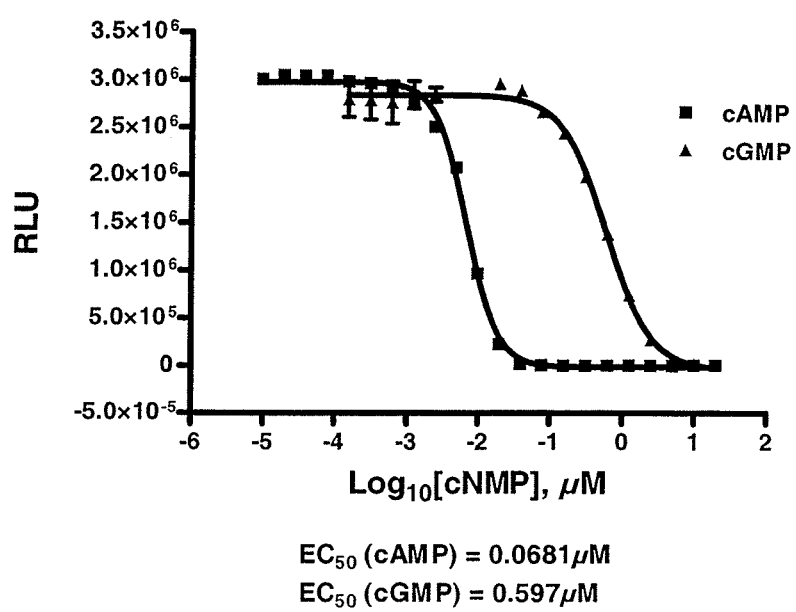
FIG. 6 demonstrates that as cyclic nucleotide concentration increases, luminescence increases in assays comprising PKA, Holoenzyme-R-II α protein kinase A, regardless of whether the cyclic nucleotide is cAMP or cGMP but with different affinities.

To demonstrate the ability of cGMP to activate PKA, side by side titrations of cAMP and cGMP were performed using the present assay system. Two-fold serial dilutions of cAMP and cGMP (initial concentration of both 40 µM) were made in Stop Buffer without ATP and IBMX, but supplemented with 2 µM ATP. Twenty-five µl of the dilutions were aliquoted into white 96-well plates, followed by the addition of 25 µl of a PKA/substrate reagent containing 100 ng/well Holoenzyme-R-II α protein kinase A, 20 µM Kemptide, 40 mM Tris HCl pH 7.5, 20 mM MgCl$_2$, and 0.1 mg/ml BSA. The reactions were allowed to incubate for 20 min. at room temperature, and 50 µl of Kinase-Glo™ Reagent was added followed by an additional 10 min. incubation. Luminescence was measured 10 min. after addition of the Kinase-Glo™ Reagent and output was recorded as RLUs (n=2) and plotted against cyclic nucleotide (cNMP) concentration using GraphPad Prism® Software Version 4.0. As shown in FIG. 6, as the concentration of the cyclic nucleotides increases the relative light units decrease. FIG. 6 demonstrates the ability of cGMP to bind to the regulatory subunits of PKA thereby releasing the active catalytic subunits, albeit at a lower affinity than that of cAMP.

Example 6—Monitoring cGMP-PDE (PDE V) Activity

Figure 7:
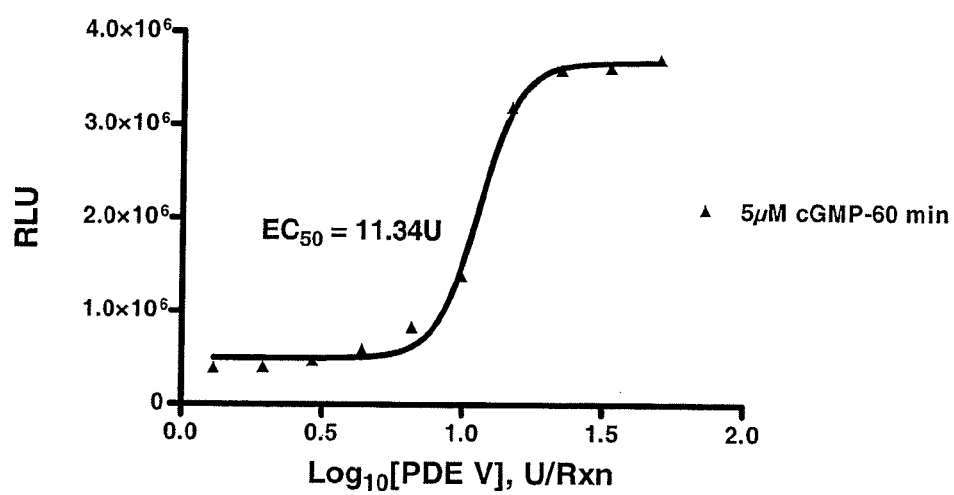
FIG. 7 shows (A) a graph demonstrating that as phosphodiesterase V concentration increases in the presence of cGMP there is an increase in luminescence in assays comprising PKA, Holoenzyme-R-II α protein kinase A and (B) a graph demonstrating that as an inhibitor of phosphodiesterase V, Zaprinast, increases in the presence of cGMP there is a decrease in luminescence in assays comprising PKA, Holoenzyme-R-II α protein kinase A.
Figure 7:
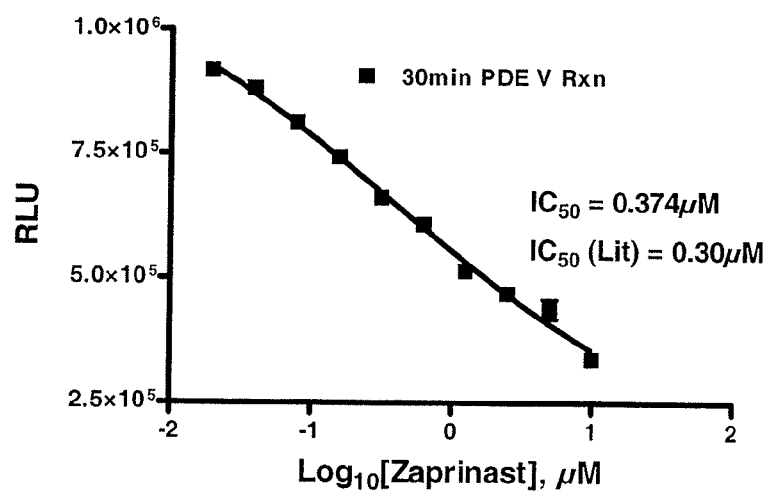

A serial dilution of phosphodiesterase PDE V starting with 50 U concentration was created in a solution containing 50 mM Tris HCl, pH 7.5, 10 mM $MgCl_2$, 0.5 mM EGTA, 0.1 mg/ml BSA, and 5 µM cGMP in a total volume of 25 µl. The enzyme reaction was allowed to progress for 60 min. at room temperature, followed by the addition of 12.5 µl of Stop Buffer. Twenty-five µl of a PKA/substrate reagent containing 100 ng/well Holoenzyme-R-II α protein kinase A, 40 µM Kemptide, 40 mM Tris HCl pH 7.5, and 30 mM $MgCl_2$ was added to the reaction wells followed by a 20 min. incubation at room temperature. An equal volume (50 µl) of Kinase-Glo™ Reagent was added, the reactions were incubated an additional 10 min., luminescence was measured and output was recorded as RLUs (n=2) and plotted against phosphodiesterase PDE V concentration using GraphPad Prism® Software Version 4.0. As can be seen in FIG. 7A, as phosphodiesterase PDE V concentration increases so does the relative luminescence of the sample. FIG. 7A demonstrates the ability of the present assay to monitor not only phosphodiesterases specific to cAMP hydrolysis, but also those specific to hydrolysis of cGMP.

Example 7—Monitoring the Activity of cGMP-PDE (PDE V) in the Presence of Inhibitors A titration of the phosphodiesterase PDE V selective inhibitor Zaprinast (Sigma) was performed. A two-fold serial dilution of Zaprinast (20 µM) was made in Stop Buffer without IBMX and ATP, supplemented with 10 µM cGMP. An enzyme solution containing PDE V was also made so that every 12.5 µl of the enzyme solution contained 15 U (Stop Buffer without IBMX and ATP) of the enzyme. An aliquot (12.5 µl) of each dilution was added to the reaction wells and an equal amount of the phosphodiesterase PDEV enzyme solution was added to start the reaction. The plate was incubated for 30 min. at room temperature, followed by addition of 12.5 µl of Stop Buffer supplemented with 1.5 mM IBMX and 4 µM ATP to stop the reaction. An equal volume of a PKA/substrate reagent containing 100 ng/well Holoenzyme-R-II α protein kinase A, 40 µM Kemptide, 40 mM Tris HCl pH 7.5, 20 mM $MgCl_2$, and 0.1 mg/ml BSA was added to each well, the plate was incubated for an additional 20 min., and 50 µl of Kinase-Glo™ Reagent was added. Luminescence was measured 10 min. after addition of the Kinase-Glo™ Reagent and output was recorded as RLUs (n=2) and plotted against Zaprinast concentration using GraphPad Prism® Software Version 4.0. As shown in FIG. 7B, as the amount of phosphodiesterase PDE V inhibitor Zaprinast increases relative light units decrease. FIG. 7B demonstrates the correlation between luminescence and Zaprinast concentration, thereby demonstrating the utility of the assay in determining potential inhibitors of the cGMP specific phosphodiesterase PDE V. FIG. 7B further displays the $IC_{50}$ for Zaprinast calculated in present experiment compared to that found in the literature (Turko 1998), again demonstrating the utility of the assay to monitor changes in activity of a cognate cGMP phosphodiesterase. Therefore, the present invention finds utility in measuring cAMP concentration and the activity of its cognate phosphodiesterase in the presence and absence of inhibitors, as well as monitoring cGMP concentration and the activity of its cognate phosphodiesterase in the presence or absence of inhibitors.

Example 8—Detection of cGMP Concentration

To determine cGMP concentration in a biological sample, the sample initially should be heated to 95° C. for 5 min, followed by addition of a cAMP selective phosphodiesterase such as PDE IV and an additional incubation at room temperature for 30 min. An aliquot of the PKA Substrate Reagent could then be added to the samples and incubated at room temperature for 20 min., followed by addition of Kinase-Glo™ Reagent (Promega Corporation, Madison Wis.). Ten minutes after addition of the Kinase-Glo™ Reagent, luminescence would be measured and output recorded (RLU) and plotted against different sample volumes. The amount of cGMP in a sample could then be determined using a graphing program such as GraphPad Prism® Software Version 4.0. and comparing sample luminescent output with that of a cGMP standard curve.

To measure activity of a cAMP or cGMP phosphodiesterases in a biological sample, the sample should be dialyzed to remove endogenous cAMP and cGMP, for example with a dialysis membrane with a 500 Da cut off. The sample that remains in the dialysis membrane would be used in the subsequent experiments. The sample would be incubated with substrates and reagents as described in the previous examples. Thus, for cAMP or cGMP phosphodiesterases, the substrates cAMP or cGMP, respectively, would be used. Detection methods could be used as previously described, and activity of the phosphodiesterase determined by comparing the detection output with that of a control.

Example 9—Detection of cAMP in Plasma Membranes

This experiment provides an exemplary method for preparing plasma membrane preparations using hypotonic or nitrogen cavitation lysis methods.

For hypotonic lysis, $3 \times 10^7$ cells were collected by centrifugation at 500×g for 5 minutes and washed twice in PBS. The cell pellet was resuspended in 10 ml of hypotonic lysis buffer (1 mM HEPES pH 7.5, 1 mM EDTA, 0.2 mM leupeptin and 40 µg/ml aprotinin), and the cell suspension was homogenized (20 strokes) using a Pyrex dounce homogenizer. In some cases, the cell suspension was homogenized three times to initiate hypotonic cell lysis. To adjust the hypotonicity in the cell suspensions, HEPES and glycerol were added to a final concentration of 25 mM and 10%, respectively, in some of the cell suspensions. To others, an equal volume of 2× buffer A (2×: 50 mM HEPES pH 7.5, 2 mM EDTA, 0.5M sucrose, 0.4 mM leupeptin and 80 µg/ml aprotinin) was added. All suspensions were homogenized by an additional 17 strokes.

For nitrogen cavitation lysis, $3 \times 10^8$ cells were collected by centrifugation at 500×g for 5 minutes and washed twice in PBS. The cell pellet was resuspended in 15 ml of buffer A (0.25 mM sucrose, 25 mM HEPES pH 7.5, 1 mM EDTA, 0.2 mM leupeptin and 40 µg/ml aprotinin). Cell suspensions were pre-equilibrated in a nitrogen cavitation bomb (Parr Instrument Company, Moline, Ill.) for 20 minutes at 350 Psi, the pressure was slowly released and the cell lysate collected.

For both lysis methods, plasma membrane fractions were collected by the following procedure. The cell lysates were subjected to low speed centrifugation (1000×g) for 10 minutes to remove cellular debris. Supernatants were collected and subjected to high-speed centrifugation (50,000× g) for 30 minutes to collect the plasma membranes. Plasma membrane fractions were resuspended in either buffer A, buffer B (25 mM HEPES pH 7.5, 1 mM EDTA, 0.2 mM leupeptin and 40 µg/ml aprotinin), or buffer B containing a final concentration of 10% glycerol.

Figure 8:
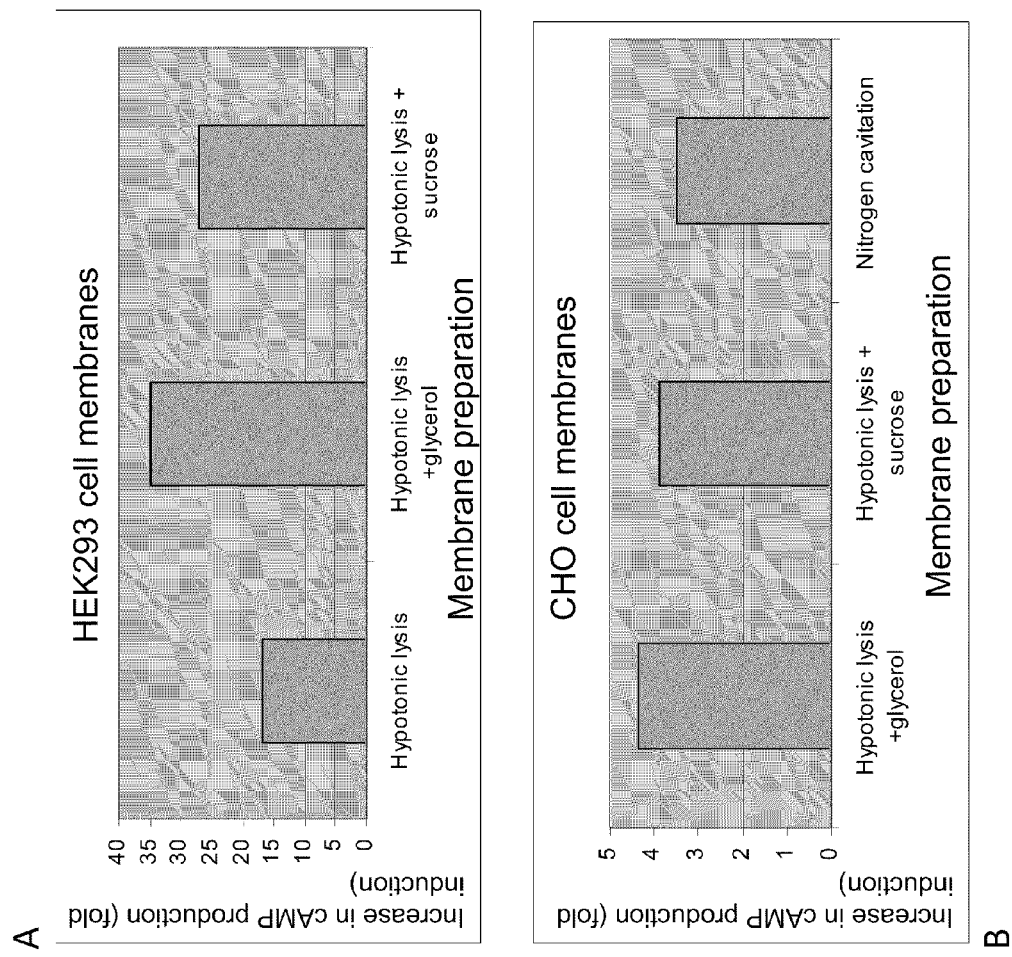
FIG. 8 demonstrates cAMP production in plasma membrane preparations from different mammalian cells prepared using hypotonic or nitrogen cavitation lysis methods; A) human embryonic kidney (HEK) 293 cells and B) Chinese hamster ovary (CHO) cells.

Different preparation methods were evaluated to determine the optimal method whereby membrane integrity is maintained and, most importantly, allowed receptor-G protein-adenylyl cyclase complexes to remain intact. FIG. 8 shows data from the testing of different membrane preparations using the different lysis methods and buffers on different cell types. Although the membrane preparations showed induced cAMP production, membranes lysed only by hypotonic lysis and resuspended in buffer B showed lower response than membranes lysed in buffer B containing glycerol or buffer A containing sucrose. No difference between the membrane preparations resuspended in buffer B containing glycerol and buffer A containing sucrose was seen.

Example 10—Detection of Forskolin Stimulated Adenylyl Cyclase Activity in Plasma Membranes Reactions were performed in a poly-D-lysine coated, white, clear bottom 96-well plate, however reactions can also be performed in a 384-well plate by decreasing the amount of added reagents proportionately. Higher density plates, such as 1536-well plates, can also potentially be used by scaling down volume additions accordingly.

A two-fold serial dilution of 250 µM forskolin in Stimulation Buffer (25 mM HEPES pH 7.5, 10 mM MgCl$_2$, 100 µM IBMX, and 0.1% Tween-20) was made. Plasma membrane preparations were prepared from the HEK293 cells stably expressing DRD1 as described in Example 4, according to the method as described in Example 9. Plasma membranes (1 µg of protein in 25 µl in Stimulation Buffer) and 1004 GDP were added to the wells of a 96-well plate and incubated at room temperature for 10 minutes. Fifteen microliters of each forskolin dilution was added to the plasma membrane preparations. A control was included by adding 15 µl of Stimulation Buffer without forskolin to several wells containing pre-incubated plasma membrane preparations. Plasma membrane preparations with or without forskolin were incubated for 15 minutes at room temperature. To detect cAMP production, 40 µl PKA/Substrate Reagent was added to each well and the reactions were allowed to incubate for an additional 20 minutes at room temperature, followed by addition of 80 µl of Kinase-Glo™ Reagent. Luminescence was read 10 minutes after addition of the Kinase-Glo™ Reagent and output was recorded as relative light units (RLU) and plotted against forskolin concentration using GraphPad Prism® Software Version 4.0.

Figure 9:
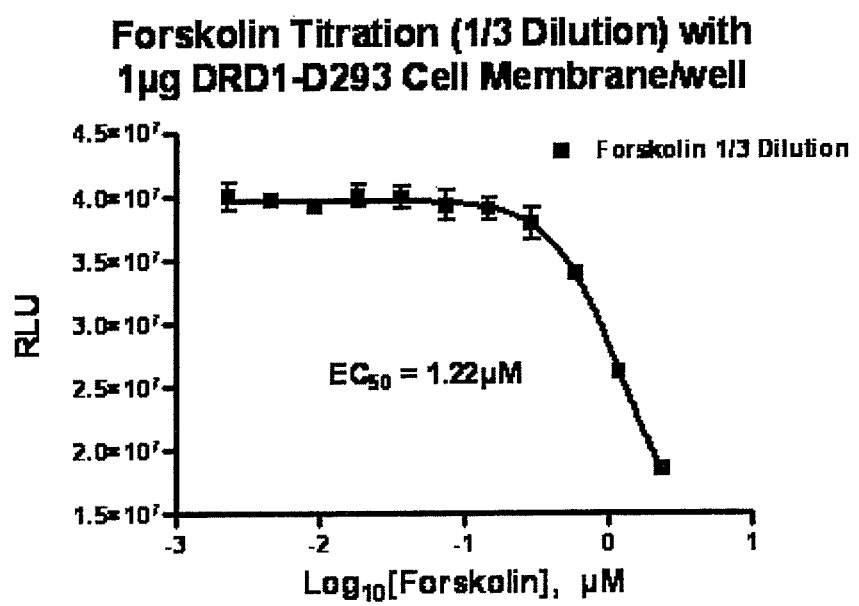
FIG. 9 shows the $EC_{50}$ for Forskolin using 1 μg of DRD1-D293 plasma membrane preparations; assays comprised PKA to detect cAMP.

As shown in FIG. 9, as forskolin concentration increases, luminescence decreases, thereby demonstrating that the present invention finds utility in detecting forskolin-stimulated adenylyl cyclase activity in plasma membrane preparations. Therefore, the present invention is capable of detecting cAMP generation in plasma membrane preparations upon induction of adenylyl cyclase by a stimulant.

Example 11—Monitoring of Dopamine Receptor D1 Activity in Response to Agonists in Plasma Membranes Experiments were conducted to demonstrate the ability of the present invention to determine the affect of agonists on adenylyl cyclase activity on the GPCR dopamine receptor D1 (DRD1) in plasma membrane preparations.

Two-fold dilutions of 10 µM stock concentrations of the agonists dopamine and SKF38393 were diluted in Stimulation Buffer containing 50 µM ATP and 0.2 µM GTP. Two-fold dilutions of a 10 µM stock concentration of the non-specific ligand for DRD1, quinpirole, were also made.

Reactions were performed in a poly-D-lysine coated, white, clear bottom 96-well plate, however reactions can also be performed in a 384-well plate by decreasing the amount of added reagents proportionately. Higher density plates, such as 1536-well plates, can also potentially be used by scaling down volume additions accordingly.

Plasma membrane preparations were prepared from the HEK293 cells stably expressing DRD1 as described in Example 4, according to the method as described in Example 7. Plasma membranes (1 µg of protein in 25 µl of Stimulation Buffer) and 10 µM GDP were added to the wells of a 96-well plate and incubated at room temperature for 10 minutes. Twenty microliters of each compound dilution was added to specific wells. Induction was carried out for 15 minutes at room temperature followed by addition of 40 µl of PKA/Substrate Reagent. The reactions were allowed to incubate for an additional 20 minutes at room temperature followed by addition of 80 µl of Kinase-Glo™ Reagent. Luminescence was read 10 minutes after addition of the Kinase-Glo™ Reagent and output was recorded as relative light units (RLU) and plotted against forskolin concentration using GraphPad Prism® Software Version 4.0.

Figure 10:
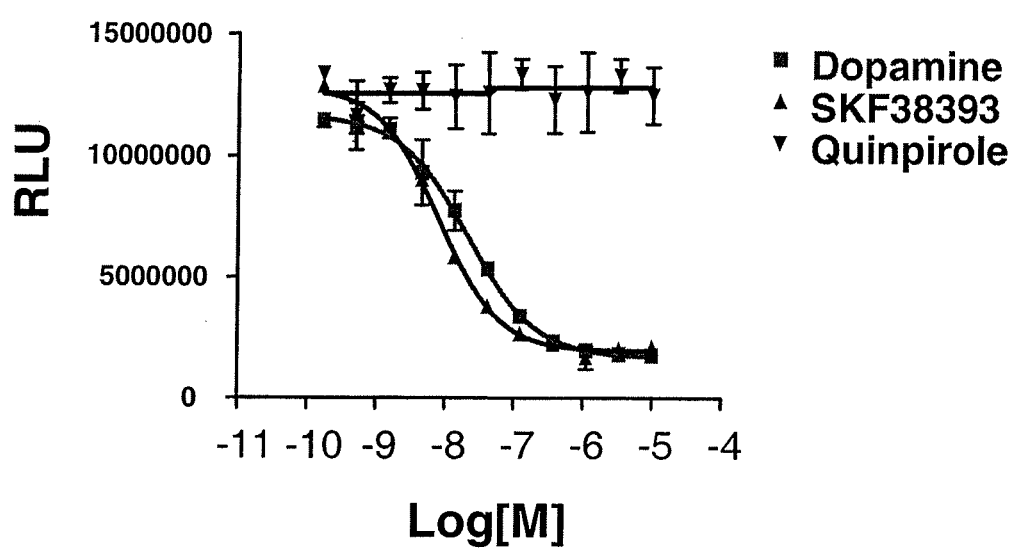
FIG. 10 demonstrates D1 receptor activation in plasma membrane preparation following activation by addition of dopamine. Activation of dopamine receptor was evaluated by measuring cAMP production using PKA.

FIG. 10 demonstrates that as agonist concentration increases luminescent signal decreases in the case of known specific DRD1 agonist (dopamine and SKF38393) but not in the case of quinpirole, a nonspecific ligand for DRD1 receptor, thereby showing that activation of DRD1 receptor can be detected in membrane preparations. Therefore, the present invention finds use in monitoring agonist/antagonist induced GPCR receptor activation in plasma membrane preparations by measuring changes in cAMP concentration.

In a similar fashion as found in Example 4, experiments with antagonists of DRD1 can be performed. For example, for testing the inhibition by an antagonist on DRD1 in plasma membranes, 10 µl of the antagonist SCH 23390 dilutions in the presence of 100 nM of the agonist SKF 38393 are added to DRD1 containing plasma membrane preparations, and the reactions are incubated for 30 min. at room temperature. The addition of PKA/Substrate Reagent and Kinase-Glo™ Reagent and subsequent incubations and readings can be carried out as described above.

Example 12—Monitoring Dopamine Receptor D2 (DRD2) Activity in Response to Agonists and Antagonists Experiments were conducted to demonstrate the ability of the present invention to determine the effect of agonists and antagonists on GPCR dopamine receptor D2 (DRD2), a $G\alpha_i$ protein coupled receptor.

A D293 cell line stably expressing DRD2 was created, using standard molecular biological techniques as described in Example 4 for DRD1.

Cells were briefly washed with phosphate-buffered saline solution to remove traces of serum and were incubated in 20 µl (96 well plate) or 7.5 µl (384 well plate) with various concentrations of D2-receptor agonists in the presence of 10 uM Forskolin in Krebs Ringer Buffer (100 uM IBMX and 100 uM Ro-20-1724). After 15 minutes of incubation at room temperature, cells were lysed using 20 µl (96-well plate) or 7.5 µl (384-well plate) of lysis buffer. After lysis for 15 minutes at RT, a kinase reaction was performed using 40 µl reaction buffer containing PKA (40 µl in 96 well and 150 in 384 well plate), and the kinase reaction was carried out for 20 minutes at room temperature. At the end of the kinase reaction an equal volume of Kinase Glo™ reagent was added and incubated for 10 min at RT, and the plates were read using a luminometer.

Figure 11A:
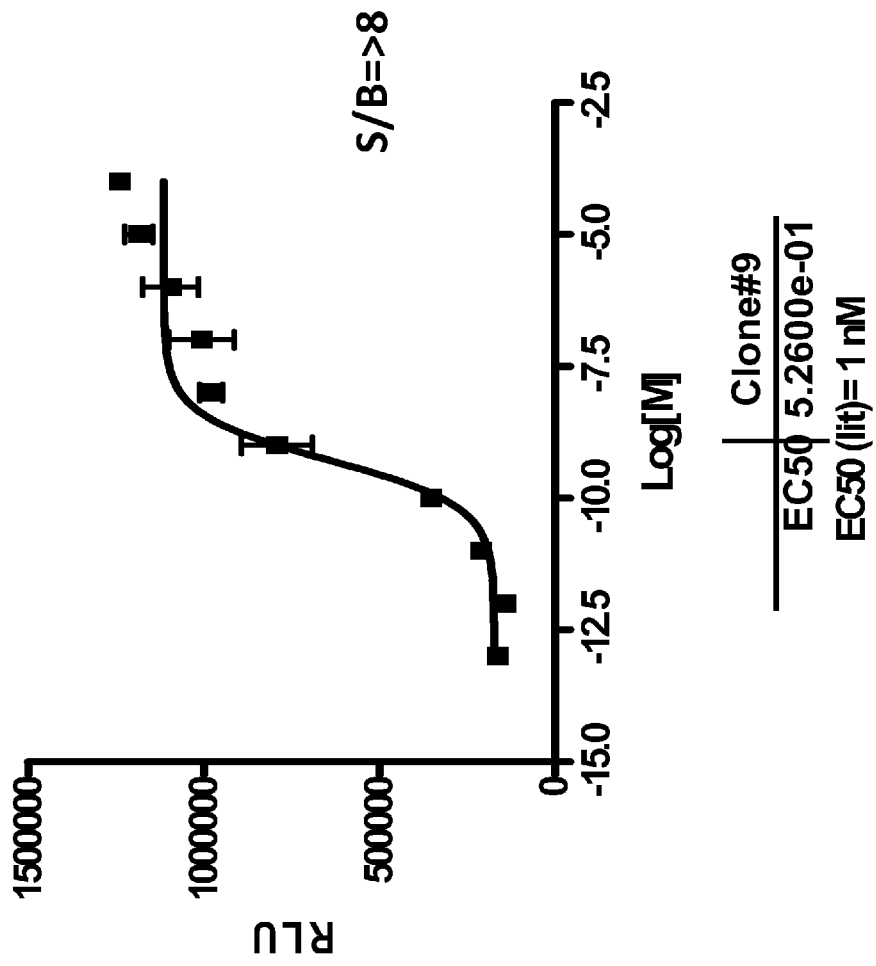
FIG. 11 shows A) an exemplary titration of Dopamine D2 receptor with the agonist Quinpirole in the presence of 10 μM forskolin using D2 stably transfected D293 cells and B) an exemplary titration of the D2 dopamine D2 receptor antagonists Raclopride in the presence of 100 nM Quinpirole and 10 uM forskolin using D2 stably transfected D293 cells; assays comprised PKA.

For the antagonist based assay, cells were incubated with 10 µM Forskolin and $EC_{80}$ concentration of agonists of D2 receptor in Krebs Ringer Buffer that contains 100 µM IBMX and 100 µM Ro-20-1724 and with or without antagonists and the assay was processed as previously described. As shown in FIG. 11A, an $EC_{50}$ of 0.5 nM for quinpirole was obtained which is similar to that reported in the literature. Similar experimental design was used to test antagonists, except that cells were incubated with 10 µM forskolin and 100 nM of the D2 agonist qunipirole, and with increasing concentrations of the antagonist raclopride. As shown in FIG. 11B, an $IC_{50}$ value of 0.8 nM for raclopride was obtained which is similar to that reported in the literature. The dopamine D2 receptor is a $G\alpha_i$ protein coupled receptor. Thus, this assay is not only capable of monitoring the modulation of $G\alpha_s$ protein coupled receptors but also the $G\alpha_i$ protein coupled receptors, thereby demonstrating the utility of the assay for HTS screening programs searching for modulators of both classes of receptors.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

The invention claimed is:

1. A method for determining the presence or amount of endogenous cyclic nucleotide in a sample comprising a cell lysate, the method comprising:
   a) contacting a sample comprising a cell lysate which may contain endogenous cyclic nucleotide, with (I) a cyclic nucleotide-dependent protein kinase capable of being activated by the endogenous cyclic nucleotide, wherein said protein kinase is Protein Kinase A and (II) a detection system, the detection system comprising:
      i) a substrate capable of being phosphorylated by the cyclic nucleotide-dependent protein kinase;
      ii) a luciferase enzyme capable of utilizing ATP to generate a bioluminescent signal; and
      (iii) ATP; and
   b) detecting or measuring the bioluminescent signal thereby determining the presence or amount of the endogenous cyclic nucleotide present in the sample, wherein the cell lysate comprises the cellular debris and fluid that is released from a cell when the cell membrane is broken apart or lysed,
   wherein the endogenous cyclic nucleotide is cAMP.

2. The method of claim 1, wherein the lysate is derived from eukaryotic cells.

3. The method of claim 1, wherein the lysate is derived from mammalian cells.

4. The method of claim 1, comprising determining the amount of the endogenous cyclic nucleotide in the sample based on the amount of change in the bioluminescent signal when compared to a standard curve of cyclic nucleotide concentration versus luminescence.

5. The method of claim 1, wherein the sample comprises plasma membranes.

6. The method of claim 1, wherein the substrate comprises SEQ ID NO:1.

7. The method of claim 1, wherein the presence or amount of cAMP present is determined by comparing the bioluminescent signal to a standard curve of cAMP concentration versus luminescence.

8. The method of claim 1, wherein the sample may contain adenylyl cyclase and further comprising determining from measuring the bioluminescent signal of step (b) the adenylyl cyclase activity present in the sample based on the presence or amount of the endogenous cyclic nucleotide.

9. The method of claim 1, wherein the sample may contain G-protein coupled receptor and further comprising determining from measuring the bioluminescent signal of step (b) the activity of a G-protein coupled receptor present in the sample based on the presence or amount of the endogenous cyclic nucleotide.

10. The method of claim 1, wherein the sample is incubated with the cyclic nucleotide-dependent protein kinase, the substrate and ATP prior to being contacted with the luciferase enzyme.

11. The method of claim 10, wherein the substrate comprises kemptide.

* * * * *

SEQUENCE LISTING

<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

Leu Arg Arg Ala Ser Leu Gly
1               5

<210> SEQ ID NO 2
<211> LENGTH: 1341
<212> TYPE: DNA
<213> ORGANISM: Homo sapiens

<400> SEQUENCE: 2
atgaggactc tgaacacctc tgccatggac gggactgggc tggtggtgga gagggacttc      60
tctgttcgta tcctcactgc ctgtttcctg tcgctgctca tcctgtccac gctcctgggg     120
aacacgctgg tctgtgctgc cgttatcagg ttccgacacc tgcggtccaa ggtgaccaac     180
ttctttgtca tctccttggc tgtgtcagat ctcttggtgg ccgtcctggt catgccctgg     240
aaggcagtgg ctgagattgc tggcttctgg ccctttgggt ccttctgtaa catctgggtg     300
gcctttgaca tcatgtgctc cactgcatcc atcctcaacc tctgtgtgat cagcgtggac     360
aggtattggg ctatctccag ccctttccgg tatgagagaa agatgacccc caaggcagcc     420
ttcatcctga tcagtgtggc atggaccttg tctgtactca tctccttcat cccagtgcag     480
ctcagctggc acaaggcaaa acccacaagc ccctctgatg gaaatgccac ttccctggct     540
gagaccatag acaactgtga ctccagcctc agcaggacat atgccatctc atcctctgta     600
ataagctttt acatccctgt ggccatcatg attgtcacct acaccaggat ctacaggatt     660
gctcagaaac aaatacggcg cattgcggcc ttggagaggg cagcagtcca cgccaagaat     720
tgccagacca ccacaggtaa tggaaagcct gtcgaatgtt ctcaaccgga aagttctttt     780
aagatgtcct tcaaaagaga aactaaagtc ctgaagactc tgtcggtgat catgggtgtg     840
tttgtgtgct gttggctacc tttcttcatc ttgaactgca ttttgccctt ctgtgggtct     900

```
ggggagacgc agcccttctg cattgattcc aacacctttg acgtgtttgt gtggtttggg    960
tgggctaatt catccttgaa ccccatcatt tatgccttta atgctgattt tcggaaggca   1020
ttttcaaccc tcttaggatg ctacagactt tgccctgcga cgaataatgc catagagacg   1080
gtgagtatca ataacaatgg ggccgcgatg ttttccagcc atcatgagcc acgaggctcc   1140
atctccaagg agtgcaatct ggtttacctg atcccacatg ctgtgggctc ctctgaggac   1200
ctgaaaaagg aggaggcagc tggcatcgcc agacccttgg agaagctgtc cccagcccta   1260
tcggtcatat tggactatga cactgacgtc tctctggaga agatccaacc catcacacaa   1320
aacggtcagc acccaacctg a                                             1341
```